(12) United States Patent
Asiri et al.

(10) Patent No.: US 11,578,033 B1
(45) Date of Patent: Feb. 14, 2023

(54) ELECTROCHEMICAL SENSOR FOR DETECTION OF HEAVY METAL IONS, AND METHODS OF PREPARATION THEREOF

(71) Applicant: King Abdulaziz University, Jeddah (SA)

(72) Inventors: Abdullah Mohamed Asiri, Jeddah (SA); Mohammed Muzibur Rahman, Jeddah (SA); Muhammad Nadeem Arshad, Jeddah (SA); Mohammad Musarraf Hussain, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/539,498

(22) Filed: Dec. 1, 2021

(51) Int. Cl.
*C07C 243/18* (2006.01)
*G01N 27/30* (2006.01)
*G01N 27/36* (2006.01)
*C07C 311/49* (2006.01)
*C07C 303/40* (2006.01)

(52) U.S. Cl.
CPC .......... *C07C 243/18* (2013.01); *C07C 303/40* (2013.01); *C07C 311/49* (2013.01); *G01N 27/308* (2013.01); *G01N 27/36* (2013.01)

(58) Field of Classification Search
None
See application file for complete search history.

(56) References Cited

PUBLICATIONS

Hussain et al. (ChemistrySelect, 2017, 2(24), p. 7455) (Year: 2017).*

Ding et al. (J. Chem. Research, Synopses, 1998, 7, p. 368-369) (Year: 1998).*

* cited by examiner

*Primary Examiner* — Sudhakar Katakam
*Assistant Examiner* — Jennifer C Sawyer
(74) *Attorney, Agent, or Firm* — WCF IP

(57) ABSTRACT

A surface modified electrode and a method of preparing the surface modified electrode are provided. The surface modified electrode includes a glassy carbon electrode and a coating of a compound of formula I disposed on the glassy carbon electrode. The present disclosure also relates to a method of preparing the surface modified electrode. The method includes depositing a slurry of the compound of Formula I on the glassy carbon electrode to form a film and coating a polymer matrix on the film to obtain the surface modified electrode. The present disclosure also relates to a method of preparing the compound of Formula I. The method includes condensing 4-bromobenzaldehyde (4-BBD) and 4-methyl-benzenesulphonylhydrazine (4-MBSH), to obtain a first mixture and precipitating the first mixture to obtain the compound of Formula I. The surface modified electrode is used in an electrochemical sensor for the detection of metal ions.

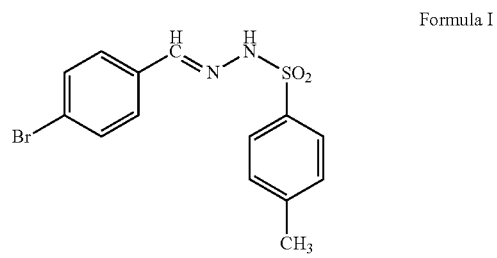

Formula I

5 Claims, 18 Drawing Sheets

ELECTROCHEMICAL SENSOR FOR DETECTION OF HEAVY METAL IONS, AND METHODS OF PREPARATION THEREOF

TECHNICAL FIELD

The present disclosure relates to a surface modified electrode, more specifically, the present disclosure relates to the surface modified electrode for use in an electrochemical sensor for the detection of heavy metal ions.

BACKGROUND

With increasing industrial activities around the world, there is a huge increase in the amount of non-biodegradable metal cations, such as cadmium, in the environment. These metal cations, like cadmium, are extensively used as coloring constituents, or for electro-plating of metals, and in rechargeable Cd—Ni batteries. Improper disposal of these metal cations leads to their increasing concentration in water, air, and plants, thereby contaminating the environment and ecological system. Ingestion of these metal cations leads to a poisonous effect on human and animal health by affecting the brain, kidneys, heart, lungs, liver, testes, and central nervous system, leading to disorders such as bone demineralization, carcinogenic effects, hypertension, nephrotoxicity, renal dysfunction, and other physiological disorders.

It is critical to detect these metal cations and efficiently treat them. Conventionally, several techniques are available for the detection of heavy metal cations such as atomic absorption spectroscopy (AAS), atomic emission spectroscopy (AES), atomic fluorescence spectroscopy (AFS), gas chromatography (GC), inductively coupled plasma mass spectrometry (ICP-MS), inductively coupled plasma emission spectroscopy (ICP-AES), inductively coupled plasma optical emission spectrometry (ICP-OES), high-performance liquid chromatography (HPLC), co-precipitation, electrochemistry, chemiluminescence, cloud print extraction, fluorescence, ion chromatography, liquid-liquid extraction, and solid-phase extraction technology. However, these techniques are time and cost intensive, require complex assembling methods, and require extra care during analysis of unsafe heavy metal cations in the laboratory. Owing to such drawbacks, there exists a need to develop simple, safe, rapid methods for detection of heavy metal ions with high selectivity and sensitivity.

SUMMARY

The present disclosure relates to a surface modified electrode. The surface modified electrode can be implemented in an electrochemical sensor for detection of metal ions. The present disclosure also relates to a method of preparing the surface modified electrode.

In one aspect of the present disclosure, a surface modified electrode is disclosed. The surface modified electrode includes a glassy carbon electrode (GCE) and a coating of a compound of Formula I disposed on the glassy carbon electrode.

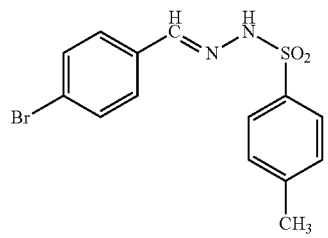

Formula I

The surface modified electrode also includes a polymer matrix configured to bind the glassy carbon electrode with the compound of Formula I. In one embodiment, the polymer matrix is a sulfonated tetrafluoroethylene-based fluoropolymer (Nafion™ OR NFN).

The surface modified electrode can be implemented in an electrochemical sensor for detection of metal ions. The electrochemical sensor is configured to determine a change in chemical information caused by the metal ion on contact with at least a portion of the surface modified electrode, and to transduce the change in chemical information associated with the metal ion to an electrical signal. In one embodiment, the metal ion is selected from a group consisting of $Cd^{2+}$, $Ce^{2+}$, $Co^{2+}$, $Mn^{2+}$, $K^+$, and $Na^+$. In another embodiment, the metal ion is a heavy metal ion. In an example, the heavy metal ion is cadmium ($Cd^{2+}$). The electrochemical sensor may be configured to detect cadmium up to 7 days.

In another aspect of the present disclosure, a method of preparing the surface modified electrode is disclosed. The method includes depositing a slurry of the compound of Formula I on the glassy carbon electrode to form a film; and coating a polymer matrix on the film to obtain the surface modified electrode. In one embodiment, the method includes depositing the slurry of the compound of Formula I on the glassy carbon electrode for a period of 1-4 hours. In another embodiment, the method includes coating the polymer matrix on the film at a temperature range of 35 to 45° C. for a period of 2-4 hours.

In yet another aspect of the present disclosure a method of preparing a compound of Formula I is disclosed. The method includes condensing 4-bromobenzaldehyde (4-BBD) and 4-methyl-benzenesulphonylhydrazine (4-MBSH) to obtain a first mixture, and precipitating the first mixture to obtain the compound of Formula I. In one embodiment, the 4-bromobenzaldehyde (4-BBD) and 4-methyl-benzenesulphonylhydrazine (4-MBSH) have a molar ratio of 1:1. In another embodiment, the method includes condensing 4-bromobenzaldehyde (4-BBD) and 4-methyl-benzenesulphonylhydrazine (4-MBSH) at a temperature range of 20-37° C. for a period of 2.5-4 hours.

The foregoing as well as other features and advantages of the present disclosure will be more fully understood from the following description, examples, and claims.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1A:
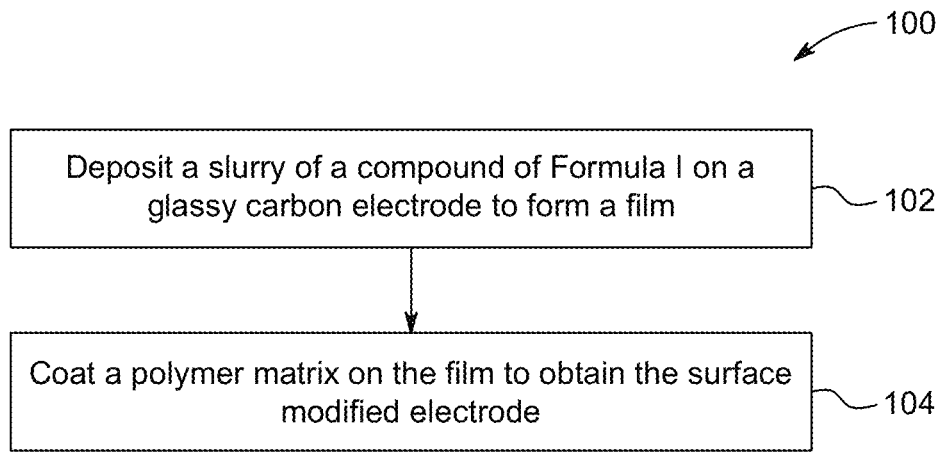
FIG. 1A is an exemplary flowchart illustrating a method for preparing the compound of Formula I (E)-N'-(4-Bromobenzyledene)-4-methyl-benzenesulfonohydrazide.

Reference will now be made in detail to specific embodiments or features, examples of which are illustrated in the accompanying drawings. A skilled artisan will appreciate that various alternate embodiments and forms may be prepared. Examples, therefore, given are only for illustration purposes without any intention to restrict the embodiments to a given set of examples. Specific functional aspects are provided merely to enable a person skilled in the art to perform the invention and should not be construed as limitations of the invention. Any method steps, and processes described herein are not to be construed as necessarily requiring their performance in the particular order discussed or illustrated, unless specifically identified as an order of performance. It is also to be understood that additional or alternative steps may be employed, unless otherwise indicated.

As used herein, "a surface modified electrode" refers to an electrode that has its surface modified for different electrochemical functions.

As used herein, "working electrode" refers to the electrode in an electrochemical cell/device/sensor on which the electrochemical reaction of interest is occurring.

As used herein, "counter-electrode", is an electrode used in an electrochemical cell for voltametric analysis or other reactions in which an electric current is expected to flow.

As used herein, an "analyte" is a substance whose chemical constituents are being identified and measured.

As used herein, an "electrochemical sensor" converts the information associated with electrochemical reactions (the reaction between the surface modified electrode and the analyte) into an applicable qualitative or quantitative signal.

The term "glassy carbon" refers herein to a non-graphitizing carbon which combines glassy and ceramic properties with those of graphite.

As used herein, "limit of detection (LOD)" is the smallest concentration of an analyte in a test sample that can be easily distinguished from zero.

As used herein, "limit of quantification (LoQ)" is the smallest concentration of an analyte in the test sample that can be determined with acceptable repeatability and accuracy.

As used herein, "linear dynamic range (LDR)" is the range of concentrations where the signals are directly proportional to the concentration of the analyte in the sample.

As used herein, "selectivity" is the quality of the electrochemical response that can be achieved without interference for any other substance.

As used herein, "sensitivity" is the change in the electrochemical response with regard to a change in the concentration of the analyte.

As used herein, a "voltammogram" is a graph that can be drawn after an electrochemical experiment. This graph has a typical, recognizable form in which the electron flow (current: I) is measured in Volt against the potential (E).

As used herein, "amount" refers to the level or concentration of one or more reactants, catalysts, present in a reaction mixture.

The use of the singular herein includes the plural (and vice versa) unless specifically stated otherwise.

The use of the terms "include," "includes", "including," "have," "has," or "having," "comprise," "comprises," "comprising" or the like should be generally understood as open-ended and non-limiting unless specifically stated otherwise.

It is understood that the order of steps or order for performing certain actions can be changed so long as the intended result is obtained. Moreover, two or more steps or actions may be conducted simultaneously.

As used herein, the term "about" or "between" refers to a ±20% to ±10% variation from the nominal value unless otherwise indicated.

Embodiments of the present disclosure are directed towards a surface modified electrode. The surface modified electrode consists of a glassy carbon electrode (GCE) modified/fabricated with the compound of Formula I. The compound of Formula I is (E)-N'-(4-Bromobenzyledene)-4-methyl-benzenesulfonohydrazide (4-BBMBSH). The surface modified electrode when implemented in an electrochemical sensor functions as a working electrode, and is effective in detection of metal ions with high selectivity, sensitivity, across a wide concentration range, with a short response time. In an embodiment, the metal ion is a heavy metal ion, like cadmium. The electrochemical characteristics of the surface modified electrode were found to be much superior in comparison to the bare electrode or the glassy carbon electrode. Although, the present disclosure describes the use of the electrochemical sensor for detection of metal ions like cadmium, the sensor of the present disclosure may be adapted for detection of other metal ions as well.

Embodiments of the present disclosure are directed to the surface modified electrode. The surface modified electrode includes a glassy carbon electrode (GCE) coated with the compound of Formula I disposed on the glassy carbon electrode. The compound of Formula I is also referred to as (E)-N'-(4-Bromobenzyledene)-4-methyl-benzenesulfonohydrazide (4-BBMBSH).

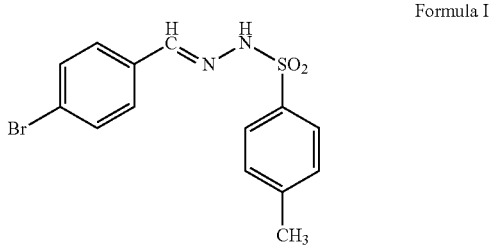

Formula I

In an embodiment, the compound of Formula I may be disposed across the length of the glassy carbon electrode with a uniform thickness or may be disposed on portions of the glassy carbon electrode. The chemical modification/fabrication of the glassy carbon electrode with the compound of Formula I may be done by any conventional methods known in the art. The chemical modification of the GCE with the compound of Formula I may result in formation of reactive groups on its surface. The surface modified electrode further includes a polymer matrix configured to bind the glassy carbon electrode with the compound of Formula I. In an embodiment, the nature of bonding between the compound of Formula I and the glassy carbon electrode, facilitated through the polymer matrix, is a covalent bond. In another example, the nature of bonding between the compound of Formula I and the glassy carbon electrode is physical adsorption. In one embodiment, the polymer matrix is a sulfonated tetrafluoroethylene-based fluoropolymer (nafion or NFN). In an embodiment, the surface modified electrode is NFN/4-BBMBSH/GCE.

The surface modified electrode can be used in an electrochemical sensor or "sensor" as a working electrode for detection of metal ions, particularly heavy metal ions. The sensor includes two electrodes, namely, the surface modified electrode or the working electrode, and a platinum wire as a counter-electrode. Although the present disclosure describes a 2-electrode system (the working electrode and the counter-electrode) in the sensor, the system may be adapted to have 3-electrodes or 4-electrodes, or multi-electrodes to detect one or more metal ions. In an example, the working electrode and the counter-electrode are connected to each other by way of electrical interconnects that allow for the passage of current between the electrodes, when a potential is applied between them. In an embodiment, the working electrode and the counter-electrode can have the same or different dimensions. In certain embodiments, the working electrode has a cross-section diameter of 1.68 millimeters, and the counter-electrode as a cross-section diameter of 0.2 millimeters. The working electrode and the counter-electrode may be arranged as readily understood and appreciated by a person of ordinary skill in the art. In an embodiment, the electrode configuration of the electrochemical sensor may be designed based on the type of metal ion to be sensed and the type of detection methodology.

The electrochemical sensor having the surface modified electrode can be used to detect a metal ion. In certain embodiments, the metal ion may be one or more selected from a group consisting of the metal ion is selected from a group consisting of $Cd^{2+}$, $Ce^{2+}$, $Co^{2+}$, $Mn^{2+}$, $K^+$, and $Na^+$. In one embodiment, the metal ion is cadmium. Although embodiments of the present disclosure are directed towards detection of cadmium ion, it may be understood by a person of ordinary skill in the art that the electrochemical sensor may be adapted for detection of other metal ions as well.

The electrochemical sensor becomes operable when the metal ion is brought in contact with the working electrode. A chemical reaction between the working electrode and the metal ion occurs causing a change in chemical information associated with the metal ion. In an embodiment, the change in chemical information could be a change in oxidation state. In other words, the metal ion may undergo a redox (oxidation-reduction) reaction resulting in loss or gain of electrons, when it is brought in contact with the working electrode. In another embodiment, the change in chemical information could be a complex formation. The electrochemical sensor is configured to determine a change in chemical information caused by the metal ion on contact with at least a portion of the surface modified electrode, and further transduce the change in chemical information associated with the metal ion to an electrical signal. In certain embodiments, the electrical signal is indicative of a concentration level of the metal ion in a sample. In some embodiment, the sample may be solid, gas or liquid. Therefore, greater the concentration of the metal ion, the stronger is the electrical signal. In one embodiment, the metal ion is selected from a group consisting of $Cd^{2+}$, $Ce^{2+}$, $Co^{2+}$, $Mn^{2+}$, $K^+$, and $Na^+$. In another embodiment, the metal ion is cadmium ion. The reactive functional groups present on the surface of the chemically modified electrode, allows for detection of cadmium with high selectivity at a short response time, owing to its high reactivity to cadmium ions. In an embodiment, the electrochemical sensor is configured to detect cadmium across a concentration range of about 8 pM. In another embodiment, the electrochemical sensor is configured to detect cadmium across a concentration range of about 10 pM. In yet another embodiment, the electrochemical sensor is configured to detect cadmium across a concentration range of about 12 pM. Electrochemical sensor analytical parameters such as sensitivity, and limit of quantification (LOQ) of the electrochemical sensor towards $Cd^{2+}$ were found from the calibration curve as 2.21519 $nA\mu M^{-1}$ $cm^{-2}$, and 334.29 mM respectively.

Referring to FIG. 1A, a method for preparing the surface modified electrode is described. In an embodiment, the method 100 includes depositing a slurry of a compound of Formula I on a glassy carbon electrode to form a film (102). In one embodiment, the slurry includes a mixture of the compound of formula I and alcohol. In another embodiment, the alcohol is a lower alcohol, such as ethanol. In some embodiments, the glassy carbon electrode may be cleaned with water and acetone before deposition of the slurry. The method includes depositing the slurry of the compound of Formula I on the glassy carbon electrode for a period of 1-4 hours (102). The method further includes coating a polymer matrix on the film to obtain the surface modified electrode (104). In one embodiment, the method includes coating the polymer matrix on the film at a temperature range of 35 to 45° C. for a period of 2-4 hours. In one embodiment, the polymer matrix is a sulfonated tetrafluoroethylene-based fluoropolymer (nafion or NFN). In certain embodiments, the polymer matrix may be added to the glassy carbon electrode in a drop-wise manner and kept open in the air so as to synchronize coating development.

Figure 1B:
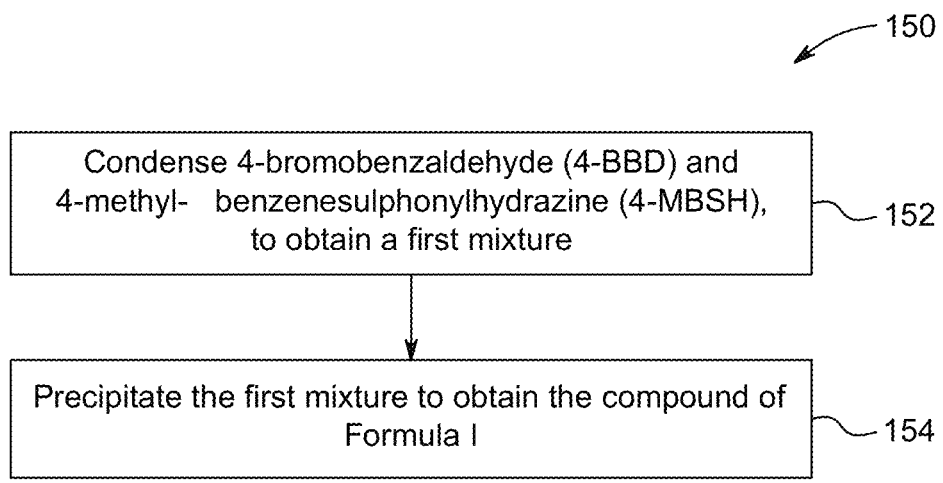
FIG. 1B is an exemplary flowchart illustrating a method for preparing the surface modified electrode.

Referring to FIG. 1B, a method for preparing the compound of Formula I is described. The method (150) includes condensing 4-bromobenzaldehyde (4-BBD) and 4-methylbenzenesulphonylhydrazine (4-MBSH), to obtain a first mixture (152). In one embodiment, the first mixture may include alcohol. In another embodiment, the alcohol may be ethanol. 4-BBD and 4-MBSH have a molar ratio of 1:1. In one embodiment, the method includes condensing 4-BBD and 4-MBSH at a temperature range of about 20° C.-37° C. for a period of about 2.5-4 hours. In another embodiment, condensing 4-4-BBD and 4-MBSH at a temperature range of about 24° C.-33° C. for a period of about 2.9-3.6 hours. In yet another embodiment, condensing 4-BBD and 4-MBSH at a temperature range of about 28° C.-29° C. for a period of about 3.2-3.4 hours. The method further includes precipitating the first mixture to obtain the compound of Formula I (154).

The surface modified electrode used in the electrochemical sensor allows for detection of cadmium ions in environmental samples with higher selectivity, sensitivity, good reliability with a short response time.

EXAMPLES

It is understood that the examples, embodiments, and teachings presented in this application are described merely for illustrative purposes. Any variations or modifications thereof are to be included within the scope of the present application as discussed.

Materials and Methods

Analytical grade chemicals for example 4-BBD, 4-MBSH, $AgNO_3$, $Al_2(SO_4)_3$, $AuCl_3$, $CaCl_2$, $CdSO_4$, $CuSO_4$, $FeCl_3$, $MgCl_2$, $ZnSO_4$, EtOH, $NaH_2PO_4$, $Na_2HPO_4$, and NF (5.0 weight % in water and a lower aliphatic alcohol that contains 45.0% water) were purchased from the Sigma Aldrich, Saudi Arabia. A stock solution of metal ions (100.0 mM and 10.0 mL) was prepared from the corresponding purchased chemical with distilled water (10.0 mL). $^1$H-NMR and $^{13}$C-NMR spectra were recorded on an ASCEND NMR machine (400 MHz) at 300 k with chemical shifts at parts per million with estimable solvent response as a reference. FT-IR spectrum was reported as neat on a NICOLET iS50 FT-IR spectrometer. UV-Visible study was carried out using Evolution 300 UV-Visible spectrophotometer (Thermo scientific). I-V examination was conducted with the detection of $Cd^{2+}$ detection in a selective point by means of NF/4-BBMBSH/GCE sensor using Keithley electrometer.

A new sulfonylhydrazone containing halogen atom was crystallized under slow evaporation for the purpose of structure elucidation, confirmation, and screened under microscope towards selection of an excellent sample. Selected needle like sample pasted over fiber glass absorbed into wax and supported with concave copper tube having magnetic base. This sample holder was mounted on Agilent super nova diffractometer outfitted with micro-focus (Cu—Mo K$\alpha$) emission for data collection and it was accomplished using Crys-Alis-Pro software at 296° K. Figures generation and refinement of the 4-BBMBSH molecule (non-hydrogen atoms) was performed using PLATON, ORTEP, and SHELXL-97 in-built with WinGX and Olex2 respectively. Aromatic carbon-hydrogen and methyl-hydrogen were positioned geometrically and treated as riding atoms with C—H=0.93 and 0.96 Å having Uiso=1.2 and 1.5 Ueq for hydrogen and carbon atoms correspondingly. N—H atoms were located through Fourier map and refined with N—H=0.82(6)–0.86 (2) Å with Uiso=1.2 Ueq for nitrogen atom. Crystal data of 4-BBMBSH molecule may be received upon application in free of charge from the Cambridge Crystallographic Data Centre.

Example 1: Process of Preparation of 4-BBMBSH

A reaction mixture of 4-bromobenzaldehyde (501.8 mg, 2.71 mmol, 1.0 equiv) and 4-methylbenzenesulfonylhydrazine (506.2 mg, 2.72 mmol, and 1.0 equiv) was added in EtOH (35.0 mL) and kept on constant stirring at room temperature for 3.0 h. The reaction mechanism is provided in Scheme 1 below. White precipitate was collected from the settled solution by removing the solvent with pipette slowly. Cold MeOH (20.0 mL) was added with the obtained precipitate and kept again at room temperature for evaporation of the solvent. Found precipitate was crystallized in MeOH to obtain 4-BBMBSH molecule as a white crystal (321.3 mg, 34.0%).

EF=$C_{14}H_{13}BrN_2O_2S$, MW=353.23, Elemental analysis=C-47.60, H-3.71, Br-22.62, N-7.93, O-9.06, S-9.08.

Figure 2A:
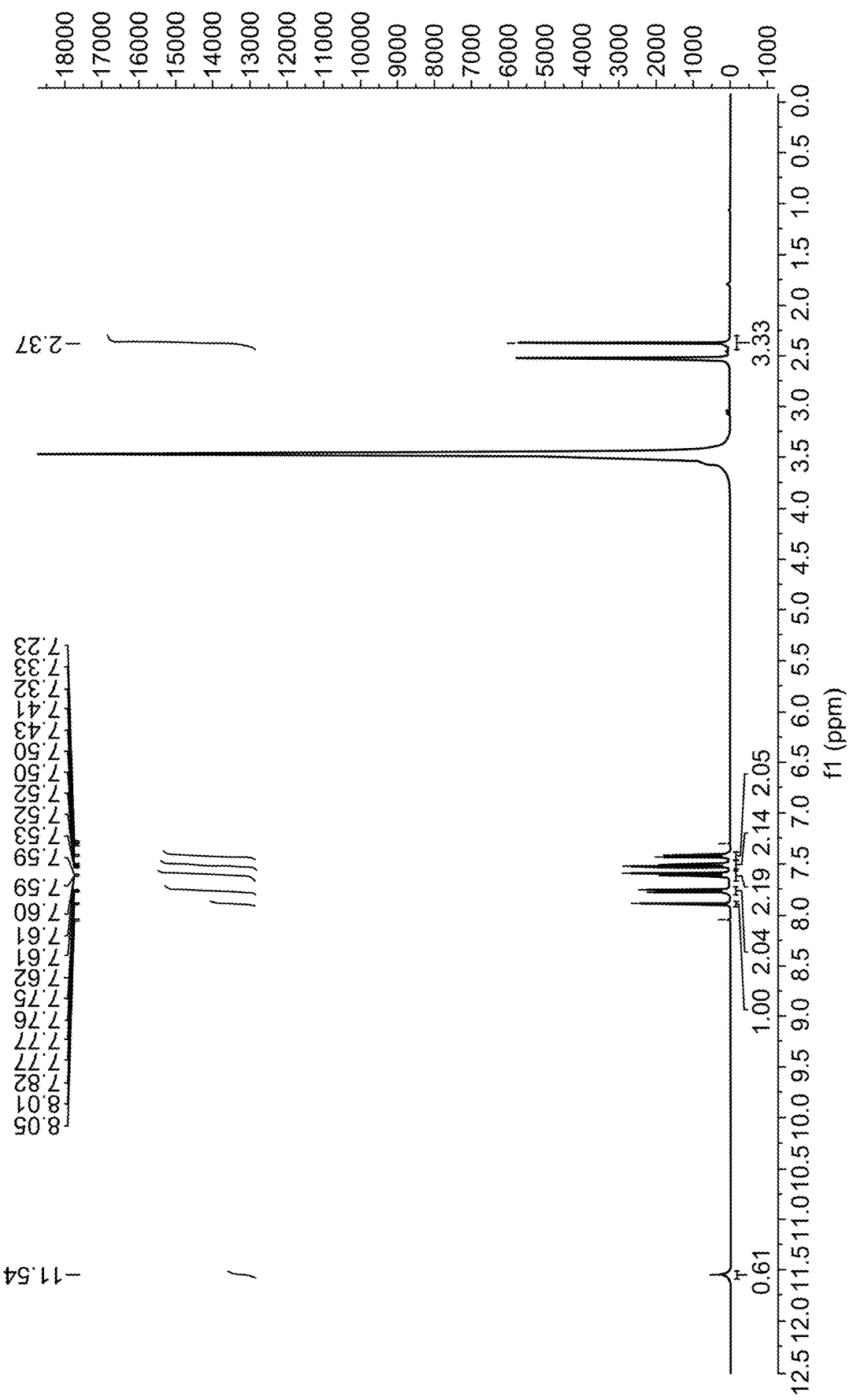
FIG. 2A is $^1$H-NMR (Nuclear Magnetic Resonance) spectra of the compound of Formula I.
Figure 2B:
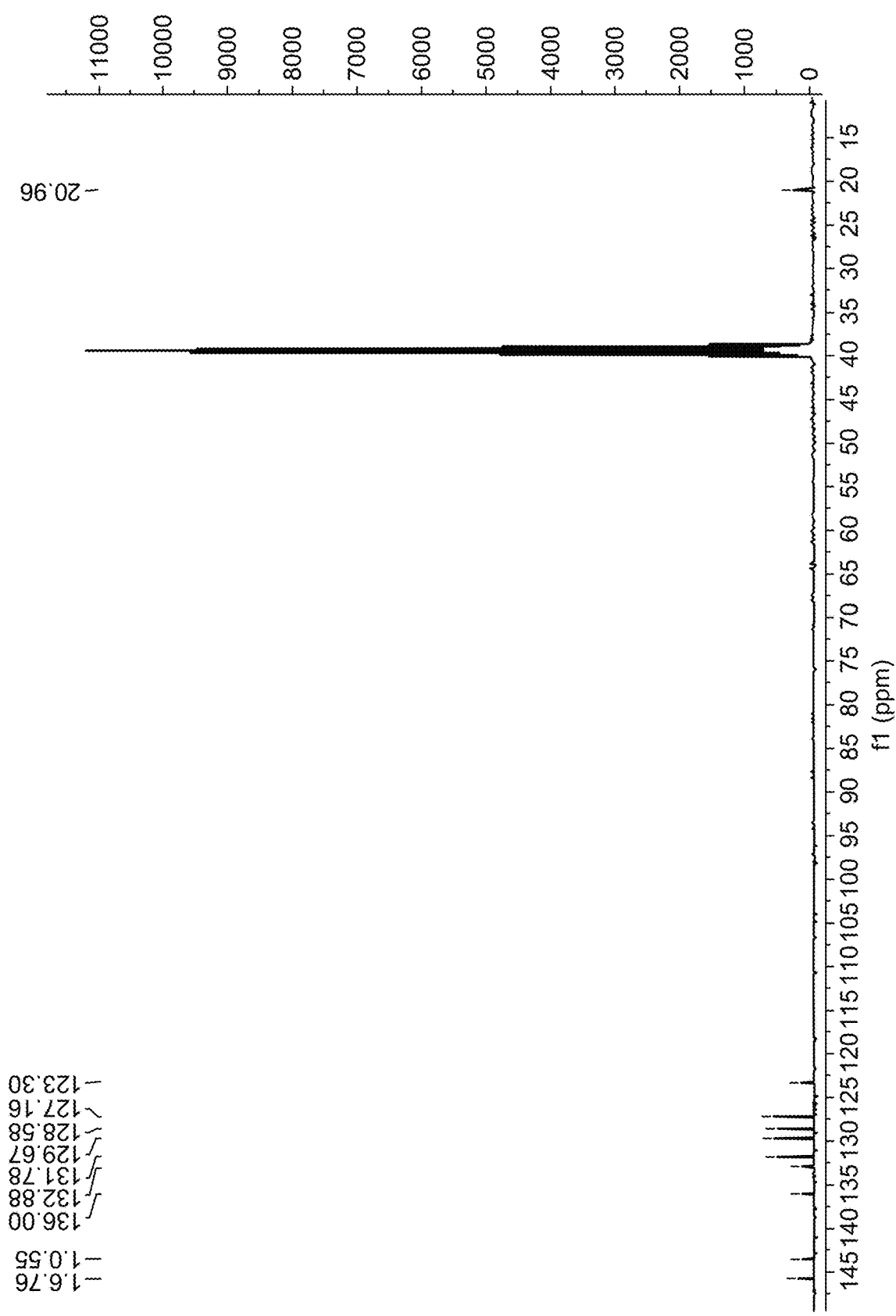
FIG. 2B is $^{13}$C-NMR of the compound of Formula I.
Figure 3A:
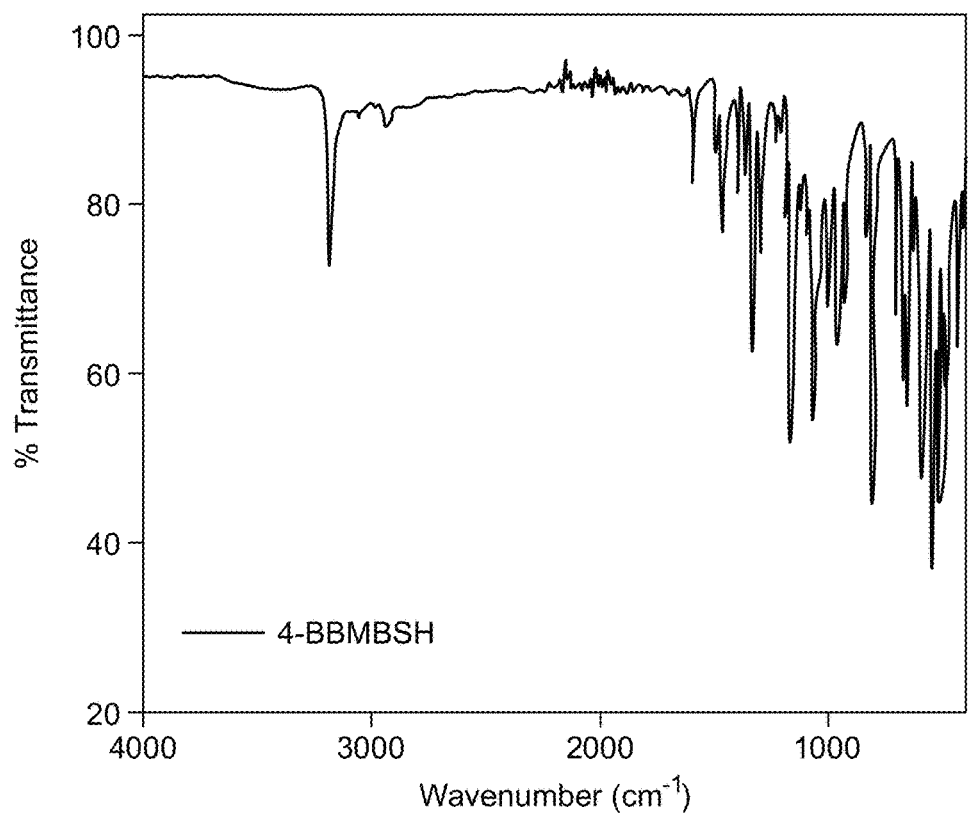
FIG. 3A shows a Fourier-Transfer Infrared Spectroscopy (FT-IR) spectrum of the compound of Formula I.
Figure 3B:
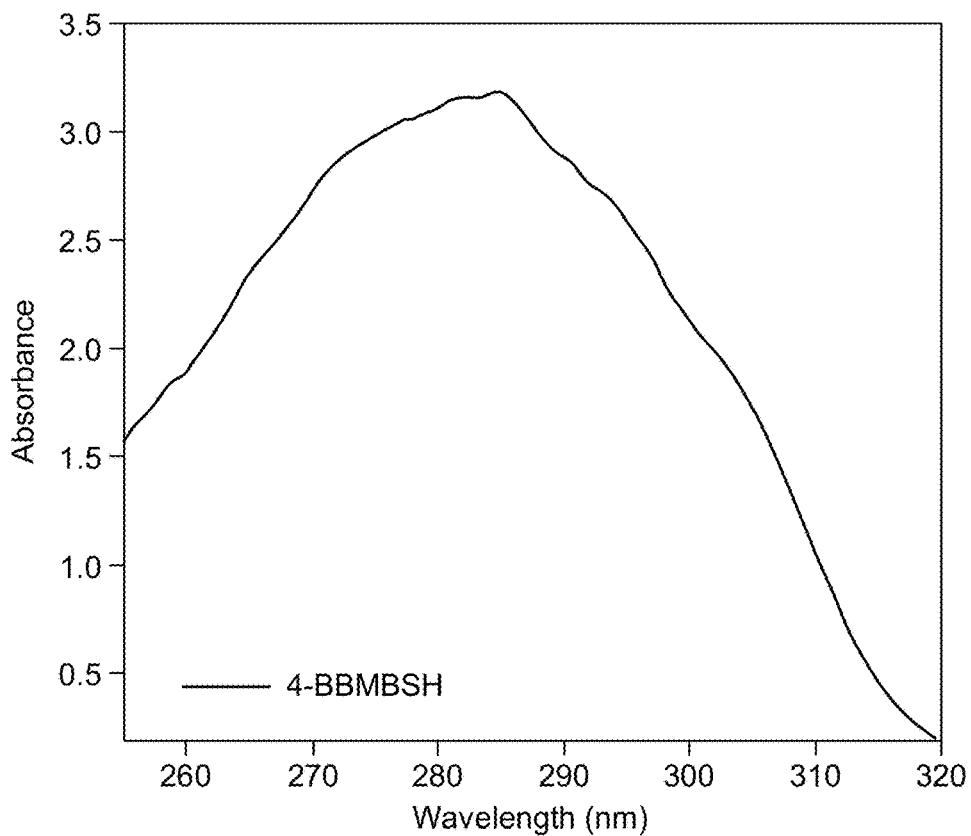
FIG. 3B shows ultraviolet (UV) spectrum of the compound of Formula I.

$^1$H-NMR (400 MHz and DMSO-d6) $\delta$: 11.54 (s, 1H), 7.89 (s, 1H), 7.80-7.73 (m, 2H), 7.67-7.56 (m, 2H), 7.56-7.47 (m, 2H), 7.42 (d, J=8.0 Hz, 2H), 2.37 (s, 3H). (FIG. 2A) $^{13}$C-NMR (101 MHz and DMSO-d6) $\delta$: 145.76, 143.55, 136.00, 132.88, 131.78, 129.67, 128.58, 127.16, 123.30, 20.96 (FIG. 2B). FTIR (neat) $v_{max}$=3194, 1600, 1468, 1345, 1198, 1078, 965, 800, 655, 600, 560, 505 (FIG. 3A). UV (DMSO, $\lambda_{max}$)=285 nm (FIG. 3B).

Scheme 1

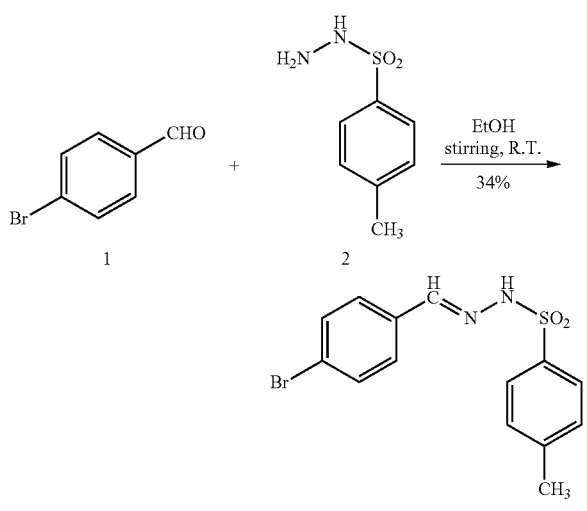

Example 2: Preparation and Modification of GCE with the Compound of Formula I (4-BBMBSH Molecule)

A series of phosphate buffer from low acidic to basic pH (5.7, 6.5, 7.0, 7.5, and 8.0) were prepared from $NaH_2PO_4$ and $Na_2HPO_4$ in distilled water. The quantity of phosphate buffer phase (10.0 mL) is kept constant throughout the entire analysis. GCE was initially cleaned with distilled water and acetone consequently and kept in open air (1.0 h) to dry completely. Prepared slurry (4-BBMBSH+EtOH) was deposited on the dried surface of GCE and kept again at open air (1.0 h) for drying. 5% nafion (NFN) is added onto the dried GCE electrodes in a drop wise manner. It is then placed again in open air (1.30 h) for synchronizing the thin-film growth in air. The surface modified GCE electrode was used as a working electrode, and Pt wire was used as a counter electrode successively to records the current-voltage signals of the metal ion determination.

Results and Discussion
Spectroscopic Studies of 4-BBMBSH Molecule

The 4-BBMBSH molecule was characterized and the structure was confirmed by means of single crystal X-ray diffraction method (SCXRDM). One N—H proton of the marked 4-BBMBSH molecule showed singlet at δ 11.54. A multiplet and one singlet were observed at δ 7.89-7.42 and 2.37 respectively indicating aromatic and three methyl protons in desired 4-BBMBSH molecule (FIG. 2A). According to $^{13}C$-NMR spectra, a good number of carbon atoms were present in the aromatic area (FIG. 2B) in 4-BBMBSH.

FT-IR spectroscopy was recorded for the functional groups in the structure (compound of Formula I or 4-BBMBSH) at 4000-400 $cm^{-1}$, the results can be observed in FIG. 3A. From the FIG. 3A it can be observed that the functional groups are presence, which confirmed the formation of the compound of Formula I. UV-Visible spectrum was also conducted in dimethyl sulfoxide (DMSO) at 200-800 nm and $\lambda_{max}$ was found at 285.0 nm (as can be observed in FIG. 3B) which is the outcome of the π-π* change of the C=NH group in the molecule 4-BBMBSH.

Figure 4A:
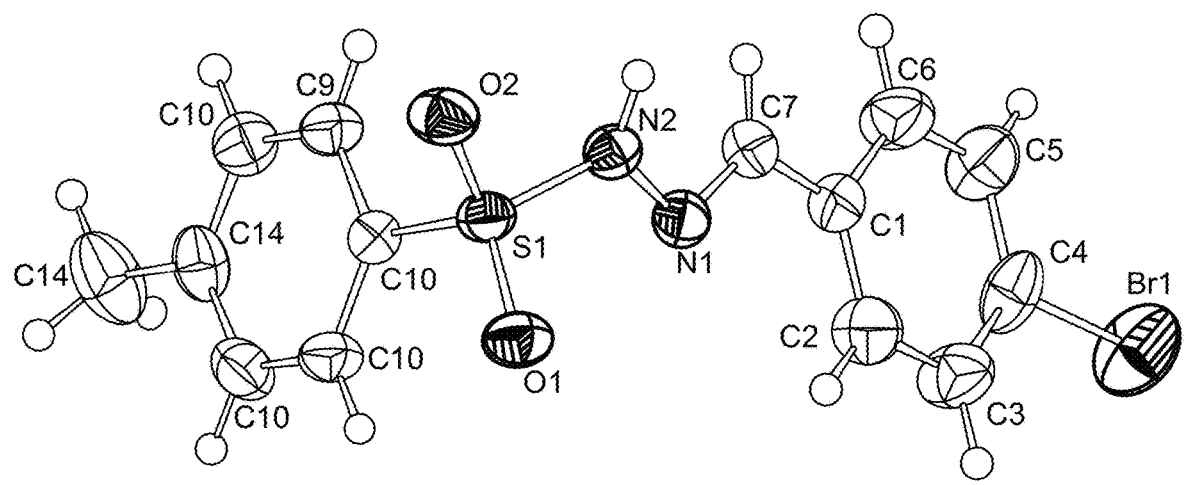
FIG. 4A shows a Oak Ridge Thermal Ellipsoid Plot (ORTEP) diagram with 50% probability of thermal ellipsoids in single crystal X-ray diffractometers (SCXRDM) analysis.
Figure 4B:
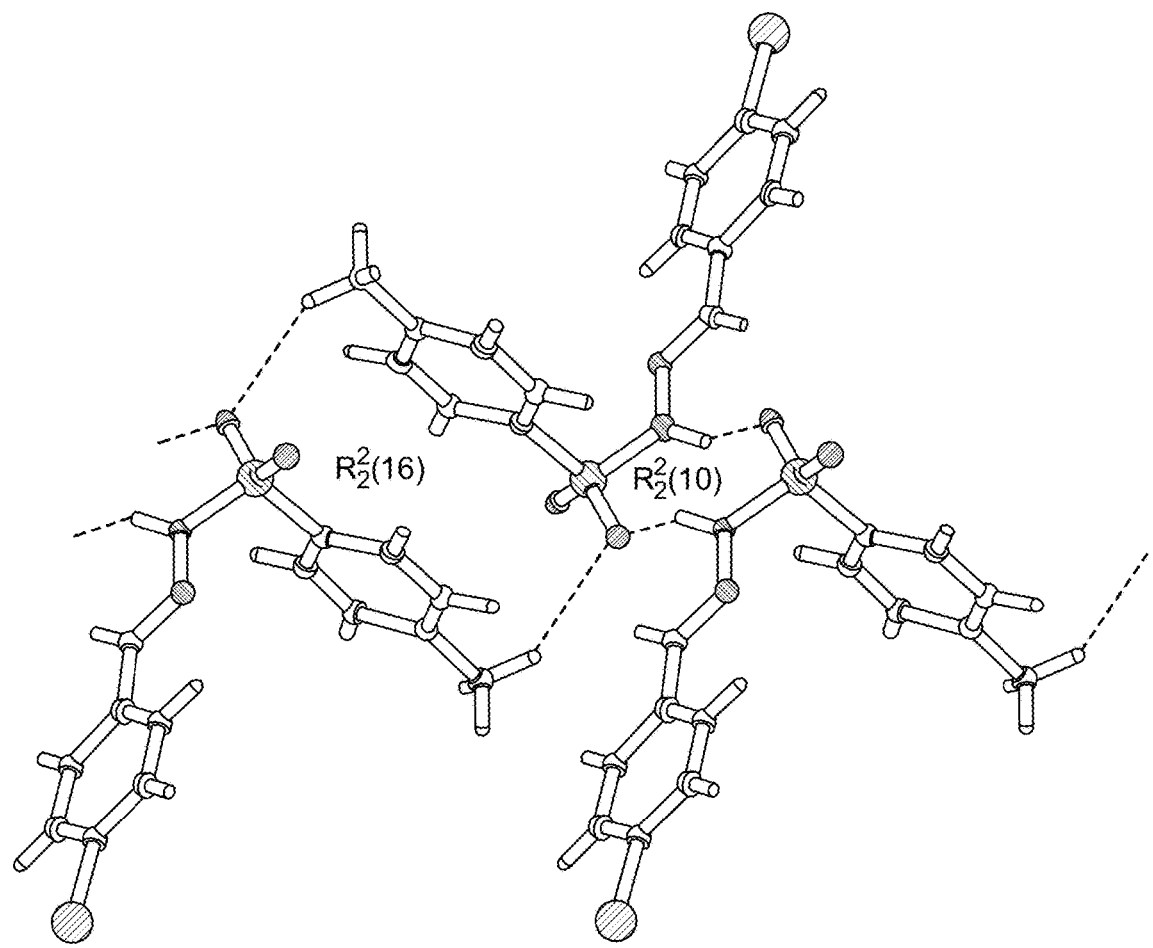
FIG. 4B is the ORTEP diagram depicting hydrogen bonding pattern of the compound of Formula I (SCXRDM analysis)

Van-der Waal's interactions give the more stability to the crystal structure of molecule and affect the physicochemical properties. Homologous structure of 4-BBMBSH was resolved with P–1 space group in triclinic model (FIG. 4A and Table 1). Distorted tetrahedral geometry around the S atoms is due to the different angles around it [<O1-S1-C8=108.8 (2)°, <O1-S1-N2=109.5 (2)°, <O2-S1-C8=109.6 (2)°, <O2-S1-N2=102.0 (2)°, <N2-S1-C8=106.7 (2)° and <O1-S1-O2=119.45 (2)° ]. The $\tau_4$ was calculated following the formula, $\tau_4=[360-(\alpha+\beta)]/141$, α and β are the largest angles around the sulphur atom, which is 0.929, confirming that the geometry of the molecule is distorted tetrahedral. A dihedral angle of 82.99 (1)° was found among the aromatic rings of the compound (FIG. 5A). Intermolecular hydrogen bonding interactions in 4-BBMBSH generate different ring motifs [$R_2^2(10)$ & $R_2^2(16)$] [39] and these interactions connect themselves to generate two different ring motifs and produce long chain along β-axis (FIG. 4B and Table 2).

TABLE 1

Molecular structure data and refinement of 4-BBMBSH

| Parameters | 4-BBMBSH |
| --- | --- |
| CCDC | 1585514 |
| ID | 17073 |
| Empirical formula | $C_{14}H_{13}BrN_2O_2S$ |
| Formula weight | 353.23 |
| Crystal system | Triclinic |
| Temperature/K | 296 (2) |
| a/Å | 5.9923 (6) |
| b/Å | 9.5124 (10) |
| c/Å | 13.0082 (14) |
| Space group | P-1 |
| α/° | 97.697 (9) |
| β/° | 95.705 (9) |
| γ/° | 92.144 (9) |
| Volume/Å$^3$ | 730.19 (13) |
| $\rho_{calc}$mg/mm$^3$ | 1.607 |
| Z | 2 |
| μ/mm$^{-1}$ | 2.96 |
| Crystal size/mm$^3$ | 0.48 × 0.09 × 0.06 |
| F(000) | 356 |
| 2θ range for data collection | 6.356 ~ 58.142° |
| Index ranges | −5 ≤ h ≤ 8, −10 ≤ k ≤ 11, −15 ≤ l ≤ 17 |
| Independent reflections | 3354 [R(int) = 0.0378] |
| Reflections collected | 5104 |
| Data/restraints/parameters | 3354/0/182 |
| Goodness-of-fit on F$^2$ | 1.013 |
| Final R indexes [I >= 2σ (I)] | $R_1$ = 0.0704 and w$R_2$ = 0.1454 |
| Largest diff. peak/hole/e Å$^{-3}$ | 0.51/−0.47 |
| Final R indexes [all data] | $R_1$ = 0.1289 and w$R_2$ = 0.1695 |
| Flack parameter | — |

TABLE 2

Hydrogen bonding pattern of 4-BBMBSH molecule 4-BBMBSH

| D | H | A | d(H-A)/Å | d(D-H)/Å | D-H-A/° | d(D-A)/Å |
| --- | --- | --- | --- | --- | --- | --- |
| N2 | H1N | O2[1] | 2.2 | 0.86 | 141.1 | 2.922(6) |
| C14 | H14C | O2[2] | 2.58 | 0.96 | 148.5 | 3.439(8) |

[1]1-X, 1-Y, -Z; [2]1-X, -Y, -Z

Bond length has been calculated for 4-BBMBSH; the results are presented in Table 3.

TABLE 3

Bond lengths of 4-BBMBSH
4-BBMBSH

| Atom | Atom | Length/Å | Atom | Atom | Length/Å |
|------|------|----------|------|------|----------|
| Br1  | C4   | 1.902(6) | C1   | C2   | 1.381(8) |
| S1   | O1   | 1.425(4) | C1   | C6   | 1.387(8) |
| S1   | O2   | 1.442(4) | C12  | C13  | 1.378(8) |
| S1   | C8   | 1.757(5) | C12  | C11  | 1.380(8) |
| S1   | N2   | 1.626(5) | N1   | C7   | 1.277(7) |
| C8   | C9   | 1.385(7) | C3   | C4   | 1.363(9) |
| C8   | C13  | 1.381(7) | C3   | C2   | 1.379(8) |
| C5   | C4   | 1.382(9) | C9   | C10  | 1.388(8) |
| C5   | C6   | 1.361(9) | C11  | C10  | 1.371(8) |
| N2   | N1   | 1.382(6) | C11  | C14  | 1.501(8) |
| C1   | C7   | 1.454(8) | —    | —    | —        |
| Br1  | C4   | 1.902(6) | C1   | C2   | 1.381(8) |
| S1   | O1   | 1.425(4) | C1   | C6   | 1.387(8) |

Bond angle has been calculated for 4-BBMBSH; the results are presented in Table 4.

TABLE 4

Bond angles of 4-BBMBSH
4-BBMBSH

| Atom | Atom | Atom | Angle/° | Atom | Atom | Atom | Angle/° |
|------|------|------|---------|------|------|------|---------|
| O1 | S1 | O2 | 119.4(2) | C7 | N1 | N2 | 114.2(4) |
| O1 | S1 | C8 | 108.8(2) | C4 | C3 | C2 | 119.1(6) |
| O1 | S1 | N2 | 109.5(2) | C8 | C9 | C10 | 119.2(5) |
| O2 | S1 | C8 | 109.6(2) | C12 | C13 | C8 | 118.7(5) |
| O2 | S1 | N2 | 102.0(2) | N1 | C7 | C1 | 122.7(5) |
| N2 | S | C8 | 106.7(2) | C12 | C11 | C14 | 120.6(6) |
| C9 | C8 | S1 | 118.8(4) | C10 | C11 | C12 | 119.0(6) |
| C13 | C8 | S1 | 120.5(4) | C10 | C11 | C14 | 120.4(6) |
| C13 | C8 | C9 | 120.7(5) | C11 | C10 | C9 | 120.8(5) |
| C6 | C5 | C4 | 119.2(6) | C5 | C4 | Br1 | 119.3(5) |
| N1 | N2 | S1 | 119.4(3) | C3 | C4 | Br1 | 120.0(5) |
| C2 | C1 | C7 | 123.6(5) | C3 | C4 | C5 | 120.7(6) |
| C2 | C1 | C6 | 117.2(6) | C3 | C2 | C1 | 121.8(6) |
| C6 | C1 | C7 | 119.1(5) | C5 | C6 | C1 | 122.0(6) |
| C13 | C12 | C11 | 121.6(6) | | | | |

Figure 5:
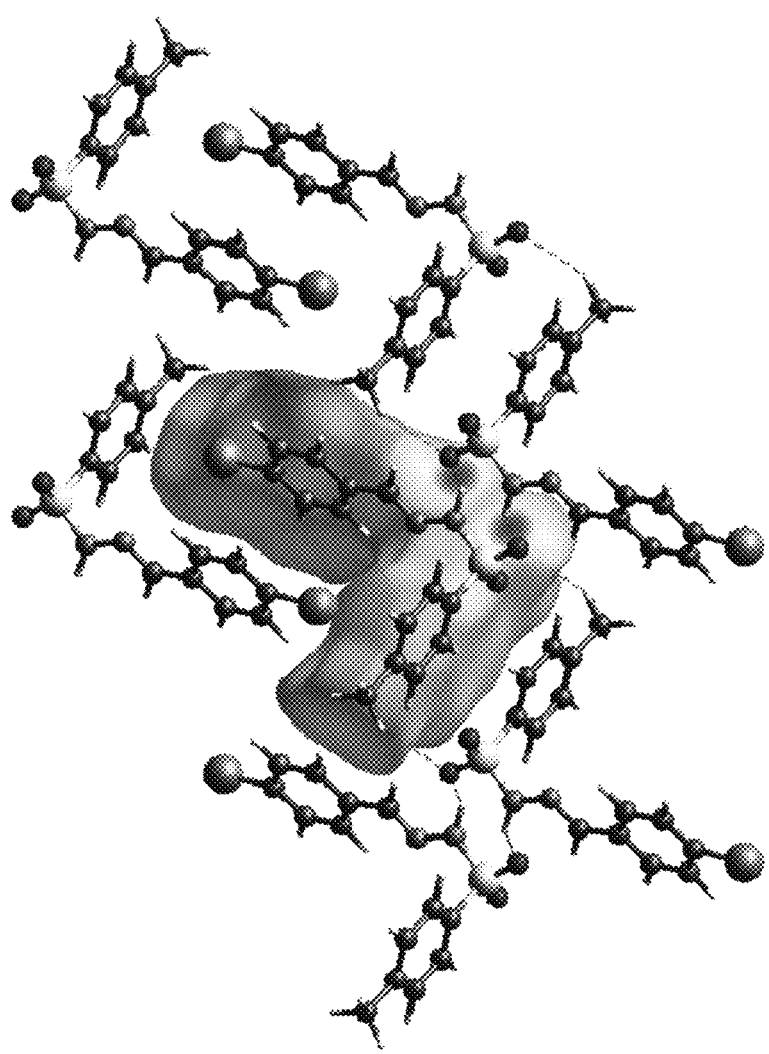
FIG. 5 shows a view along a-axis of Hirshfeld surface (SCXRDM analysis) mapped on normalized mode ($d_{norm}$)
Figure 6A:
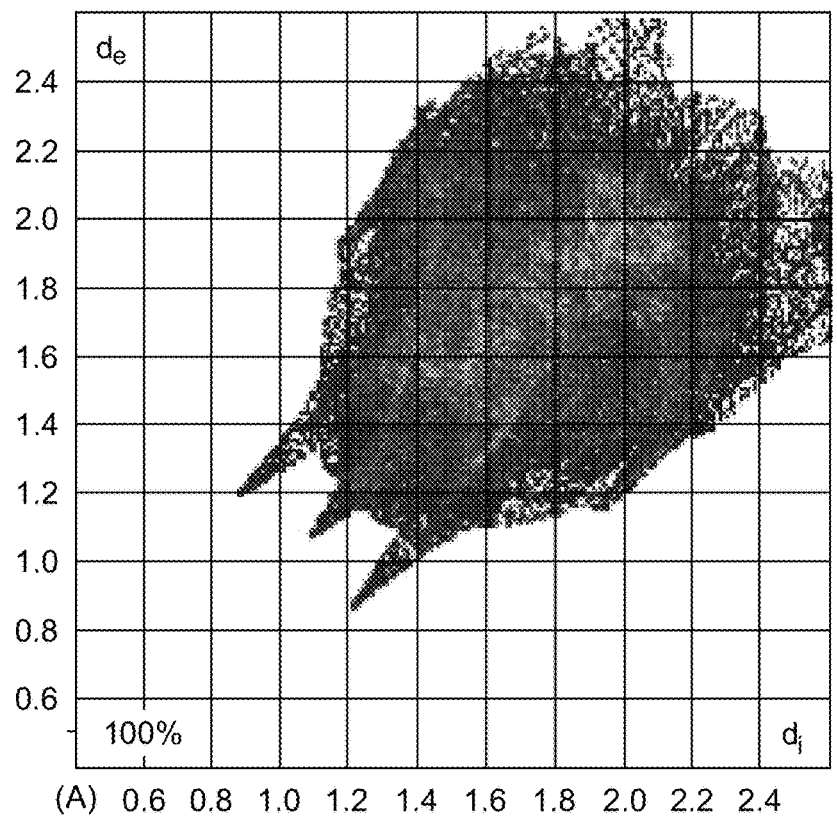
FIG. 6A-6E depicts a two dimensional fingerprint plot and contribution of interaction of individual or all contributing atoms in the compound of Formula I (SCXRDM analysis)
Figure 6B:
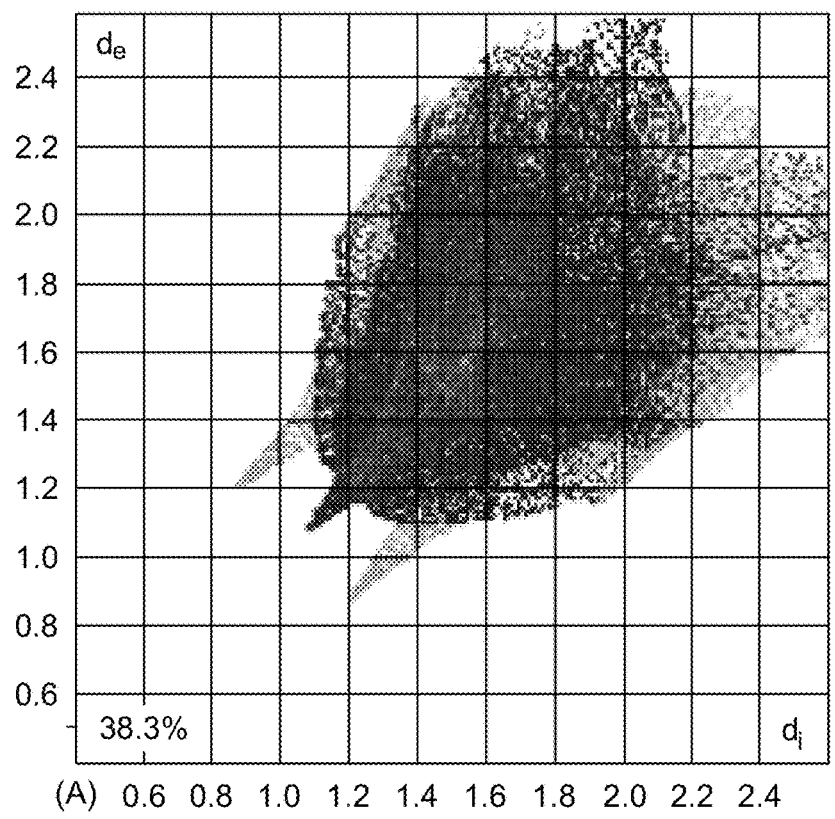
Figure 6C:
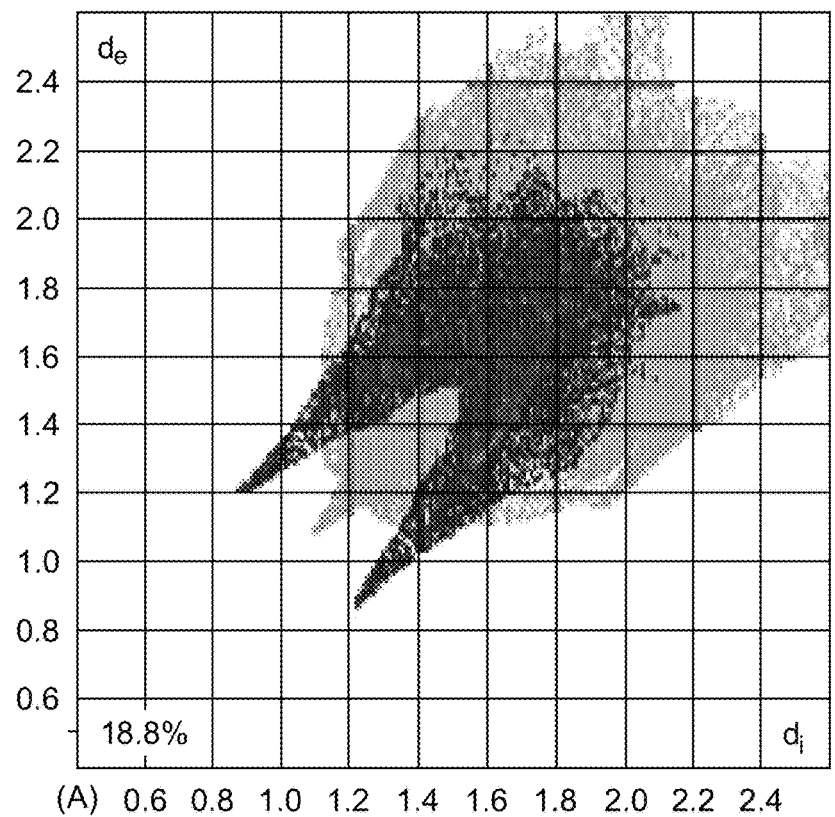
Figure 6D:
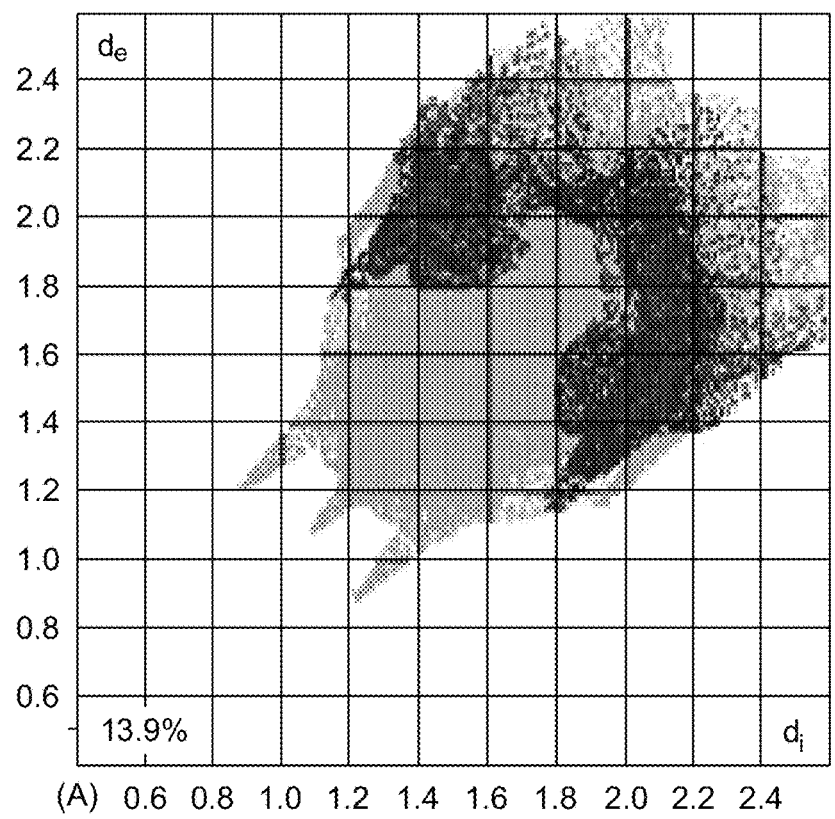
Figure 6E:
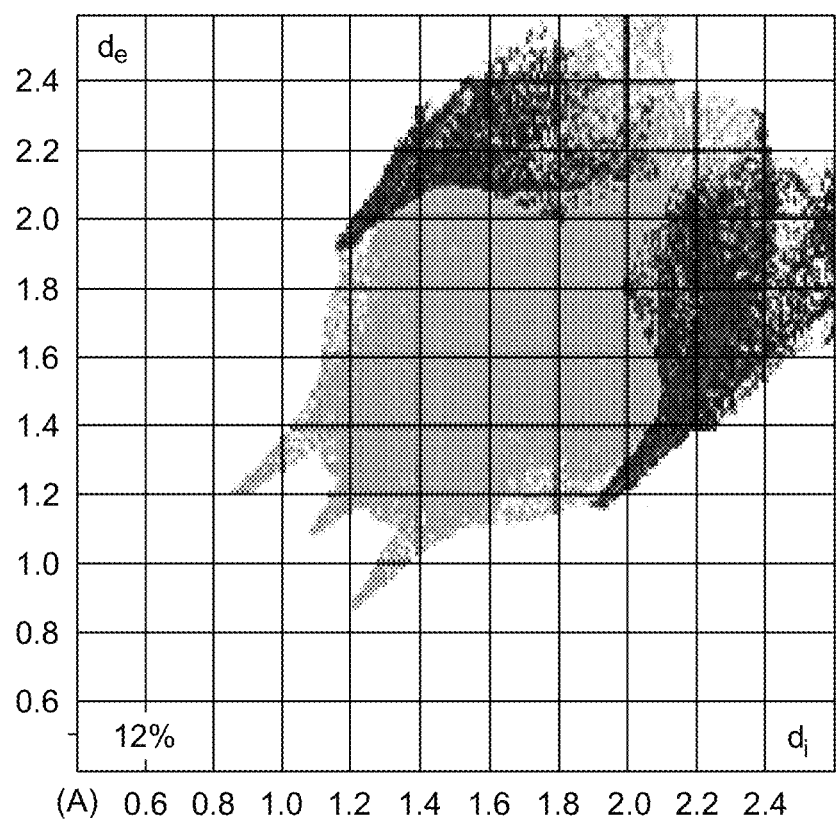

The Hirschfield surface analysis of the compound of Formula I has been measured to understand the intermolecular interactions (FIG. 5). The measurement was done using Crystal-Explorer 17.5 and FIG. 5 shows the normalized contact distance ($d_{norm}$) map as well as the hydrogen bonding interactions. This ($d_{norm}$) map clearly suggests that there is N—H . . . O type hydrogen bonding interaction (Table 1). The map also shows represent the hydrogen donor and hydrogen acceptor regions on molecule under study (FIG. 5). The two dimensional finger print plots were also studied and it is found that H—H contact is a major contributing factor in the Hirschfield surface generation (38.3%), as can be observed in the FIG. 6A. The contributing portions for O—H/H—O, C—H/H—C, and Br/H—Br are 18.8%, 13.9%, and 12%, respectively (FIG. 6B-6E).

Electrochemical Application of NF/4-BBMBSH/GCE Sensor

Figure 7:
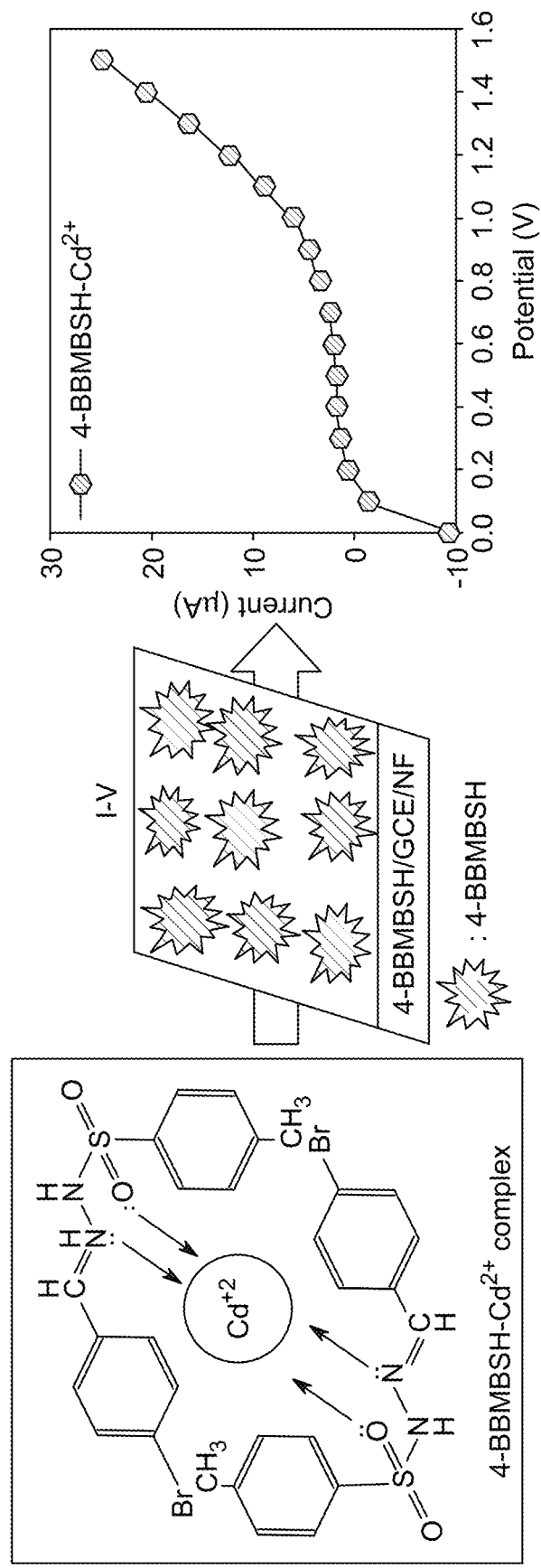
FIG. 7 depicts a proposed electrochemical mechanism of cadmium ions at the surface modified electrode, and also depicts outcomes of I-V experimental results.
Figure 8A:
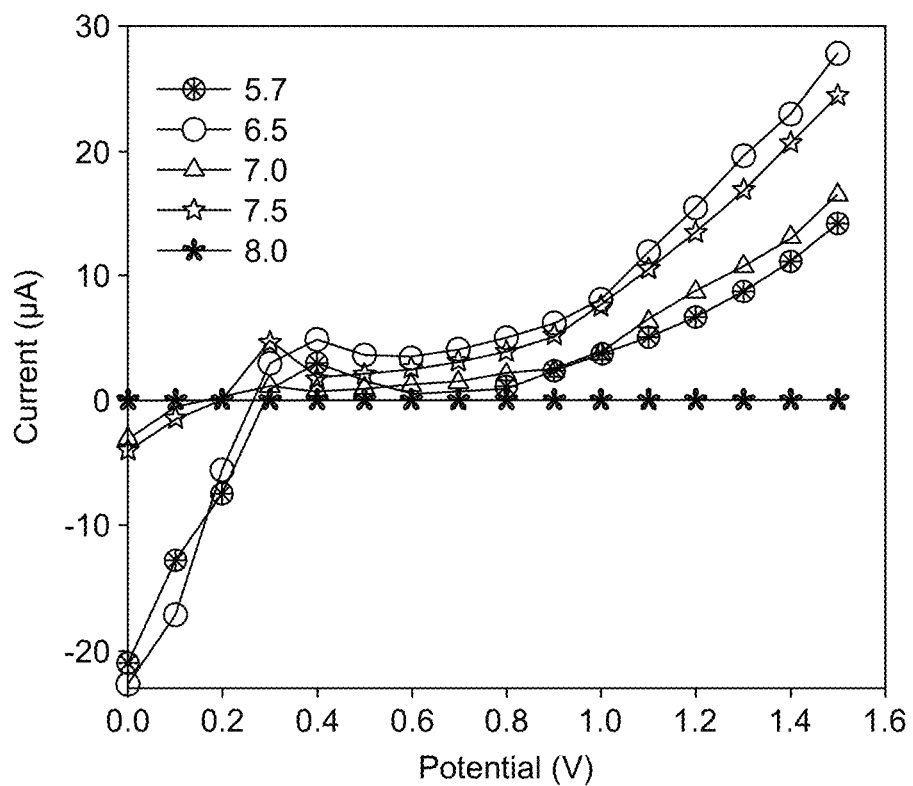
FIG. 8A is a voltammogram depicting the effect of pH on the surface modified electrode in the presence of cadmium ions within a pH range of 5.7-8.0.

FIG. 7 depicts a proposed electrochemical mechanism of cadmium at surface modified electrode, and also depicts outcomes of I-V experimental results. The electrode (GCE) was fabricated with the compound of Formula I with the polymer matrix to function as a sensor (NF/4-BBMBSH/GCE sensor) for metal ion detection. The sensor was further examined for the selective detection of the target metal ion, particularly cadmium, in phosphate buffer. Electrochemical response of the sensor was dynamically altered due to adsorption of $Cd^{2+}$, possibly through the formation of 4-BBMBSH-$Cd^{2+}$ complex. This change in chemical information (loss of electrons) caused by $Cd^{2+}$ on contact with at least a portion of the working electrode causes the sensor to transduce the change in chemical information associated with $Cd^{2+}$ to an electrical signal. Further, real electrical responses of $Cd^{2+}$ are investigated by simple and reliable I-V technique with electrode of the present disclosure, which can be observed in FIG. 7. A significant amplification in the current response with applied potential is noticeably confirmed. This is possibly due to the presence of reactive functional groups present on the surface modified electrode that causes adsorption of cadmium ion with improved sensitivity, and enhanced the current responses against potential during the I-V measurement at room conditions.

pH is an important factor affecting the performance of surface modified electrode. The effect of pH of cadmium ion on the sensing ability of the surface modified electrode was further evaluated, and the results of this experiment are presented in FIG. 8A. Electochemical analysis with the sensor was examined in phosphate buffer (amount=10.0 ml) at various pH conditions—ranging from lower acidic to little basic condition (pH=5.7-8.0). The pH was adjusted using chemicals known in the art. All other process parameters were kept identical while performing the experiment. The current response at different pH was noted. From FIG. 8A, it can be observed that although the electrochemical sensor is effective in detection of cadmium ion at a wide range of pH values, best results were observed at a slightly acidic or neutral pH values. A higher electrical response was recorded at pH=6.5 with the sensor of the present disclosure. From these findings it is evident that the electrode exhibits superior sensitivity with enhanced current response at pH 6.5, because of the higher rate of electron transfer at pH 6.5.

Figure 8B:
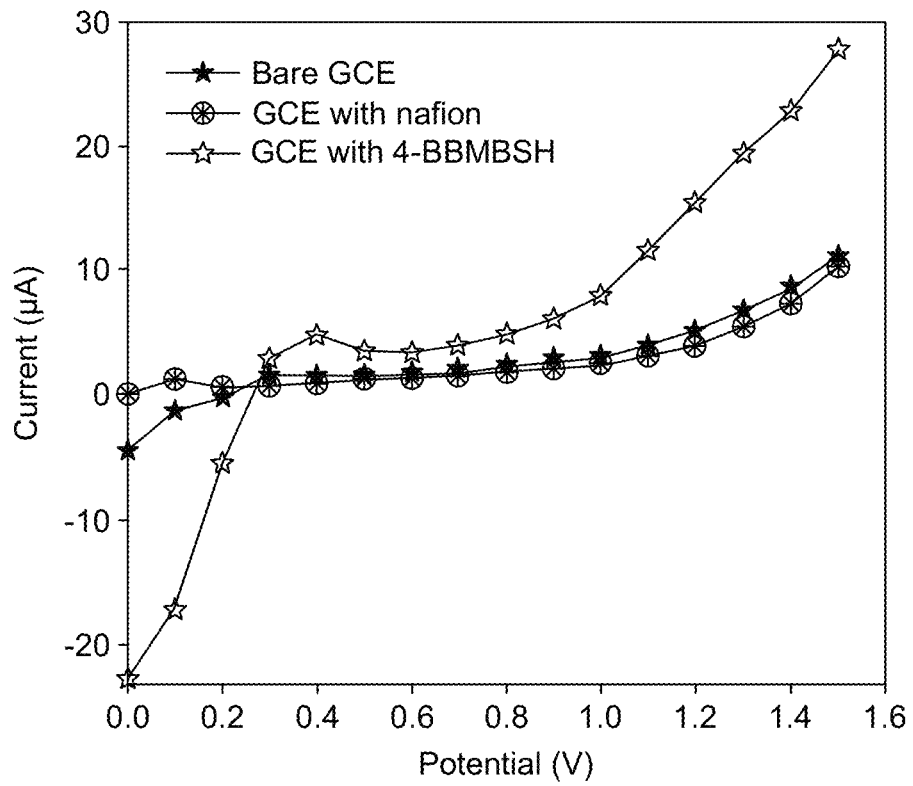
FIG. 8B is a voltammogram comparing the electrochemical behavior with different electrodes: i) a bare electrode (glassy carbon electrode), ii) glassy carbon electrode with a polymer matrix (nafion) and iii) the surface modified electrode, in sensing cadmium ions.

Further, the current response of the surface modified electrode was compared to that of a bare/uncoated electrode (bare GCE), and GCE coated with nafion. The results of this study are presented in FIG. 8B. The current response was found to be the strongest with the fabricated electrode, in comparison the bare/uncoated electrode (bare GCE), and GCE coated with nafion.

Figure 8C:
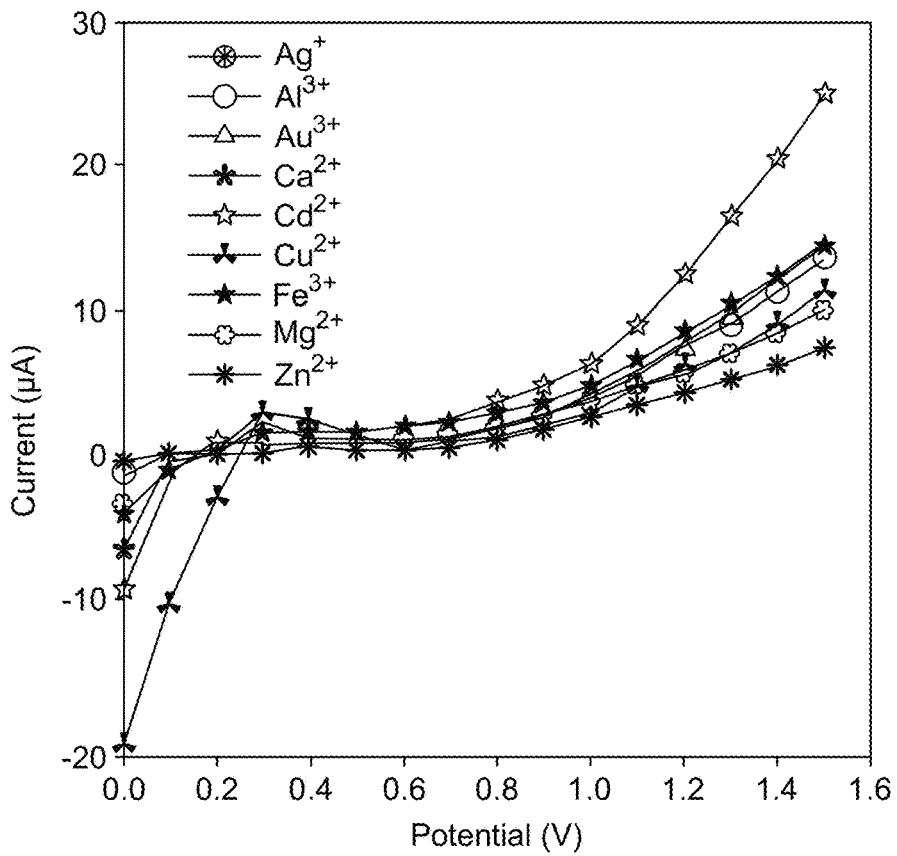
FIG. 8C illustrates a I-V graph depicting the selectivity of the surface modified electrode towards various metal ions.

One of the most essential and desirable features of an electrochemical sensor lies in its ability to distinguish the metal ion of interest, from other metal ions, even at very low concentrations, from interfering chemicals. In other words, the electrochemical sensor ought to be selective and sensitive. To assess the selectivity of the electrode, metal ions (25.0 μL and 1.0 μM) such as $Ag^+$, $Al^{3+}$, $Au^{3+}$, $Ca^{2+}$, $Cd^{2+}$, $Cu^{2+}$, $Fe^{3+}$, $Mg^{2+}$, and $Zn^{2+}$ in phosphate buffer phase (pH=6.5, 10.0 mL, and 100.0 mM) was investigated. The results of this study are presented in FIG. 8C. From the FIG. 8C, it can be observed that although the selectivity towards iron and aluminium ions was found to be moderate, best amperometric response was observed, given all other reaction conditions kept constant, was observed with the cadmium ions at applied potential range of 0.1-1.5 V.

Figure 8D:
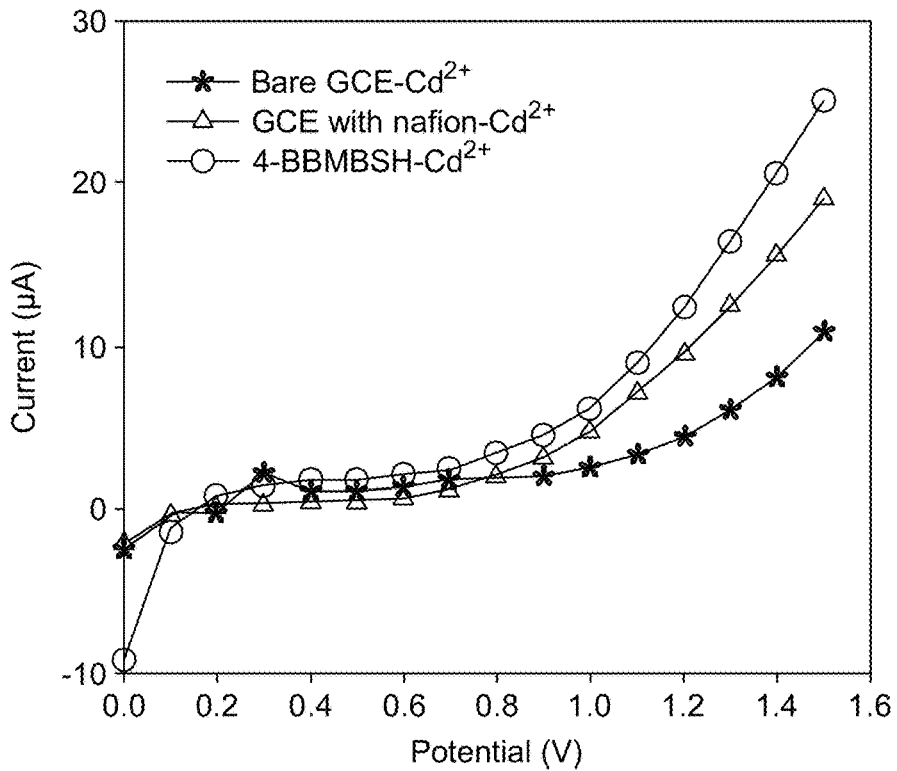
FIG. 8D is a control experiment comparing the sensing ability of cadmium ions at 1 μM concentration with different electrodes: i) a bare electrode (glassy carbon electrode), ii) glassy carbon electrode with a polymer matrix (nafion) and iii) the surface modified electrode, in sensing cadmium ions.

A control experimentation at 25.0 μL and 1.0 μM cadmium ion was performed in phosphate buffer (10.0 mL, pH=6.5, and 100.0 mM) with the bare/uncoated electrode (bare GCE), GCE coated with nafion, and NF/4-BBMBSH/GCE sensor. The results of this study are presented in FIG. 8D. From the FIG. 8D, it can be observed that a highest current response was observed with the NF/4-BBMBSH/GCE sensor in comparison with other sensors confirming the superiority of the NF/4-BBMBSH/GCE sensor.

Figure 9:
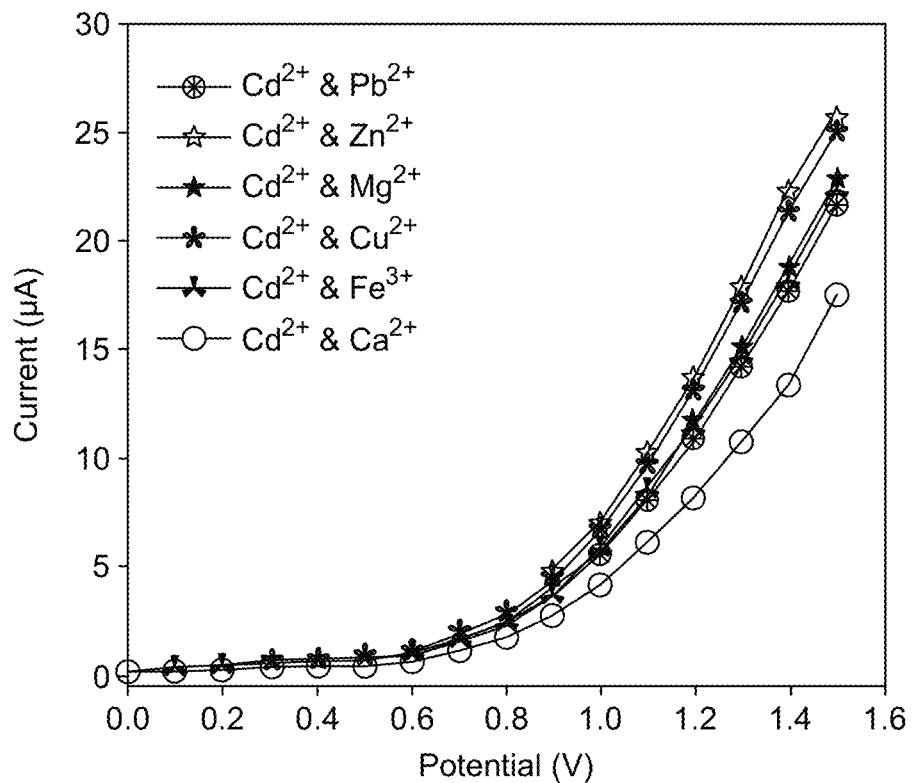
FIG. 9 depicts electrochemical responses with the electrochemical sensor in presence of various cations along with cadmium ion.

FIG. 9 depicts the influence of other cations in the presence of cadmium ions; the electrochemical responses are observed with the electrochemical sensor. In presence of other cations, the sensor response was found to be almost similar, not same. The performance of the sensor for its ability to detect cadmium in the presence of an other cations like lead, zinc, magnesium, copper, iron, and calcium was studied. The current response was found to be similar with each study, despite the presence of other cations, suggesting that the selectivity of the sensor towards cadmium.

Figure 10:
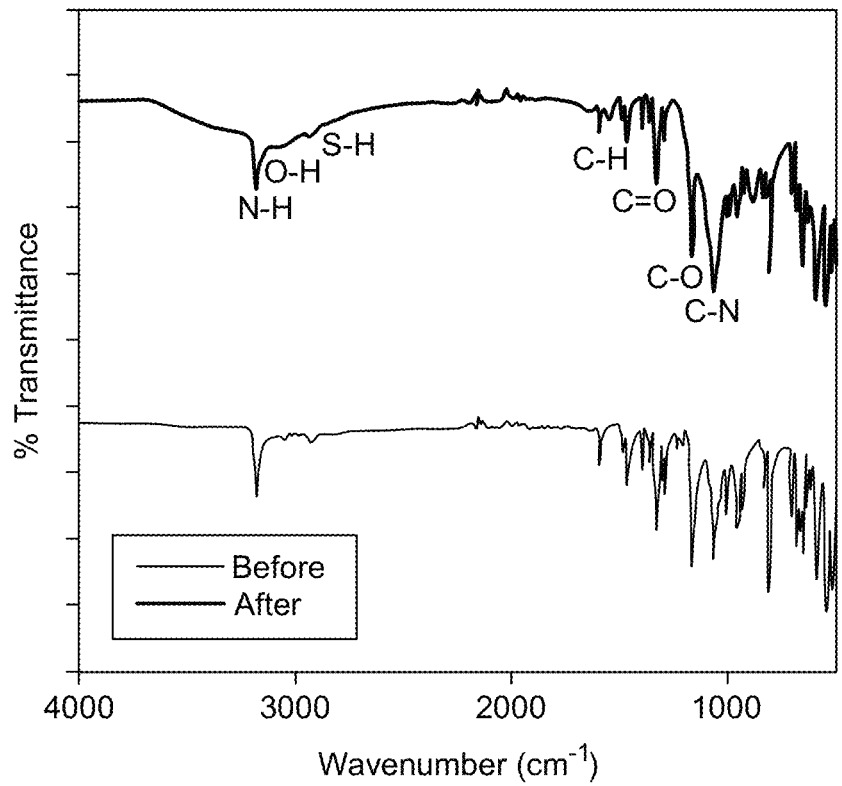
FIG. 10 depicts a comparative FT-IR spectra of the surface modified electrode before the detection of cadmium ions, and after the detection of cadmium ions.

The FT-IR is an analytical technique based on the interaction with the functional groups in 4-BBMBSH compound with any other metal ions. FT-IR measurement of the surface modified electrode was preformed before and after adding of cadmium ion and the results were compared, as can be observed in FIG. 10. In the FT-IR, absorptions are exhibited by the fundamental vibrations of the —CH, —NH, —OH, —SH groups, among others. The FT-IR region can lead to quantitative analysis, since the absorbance of the 4-BBMBSH sample is proportional to the number of functional groups. Here, the interaction of existing functional groups in 4-BBMBSH contributing to the formation of absorption bands at specific wave-numbers are compared and indicated in the same spectrum. After interaction/detection of cadmium ions, the absorption bands of functional groups in 4-BBMBSH compound were found to be slightly changed or shifted to the higher energy level, indicating or confirming the interaction between the functional groups and the cadmium ion.

Figure 11A:
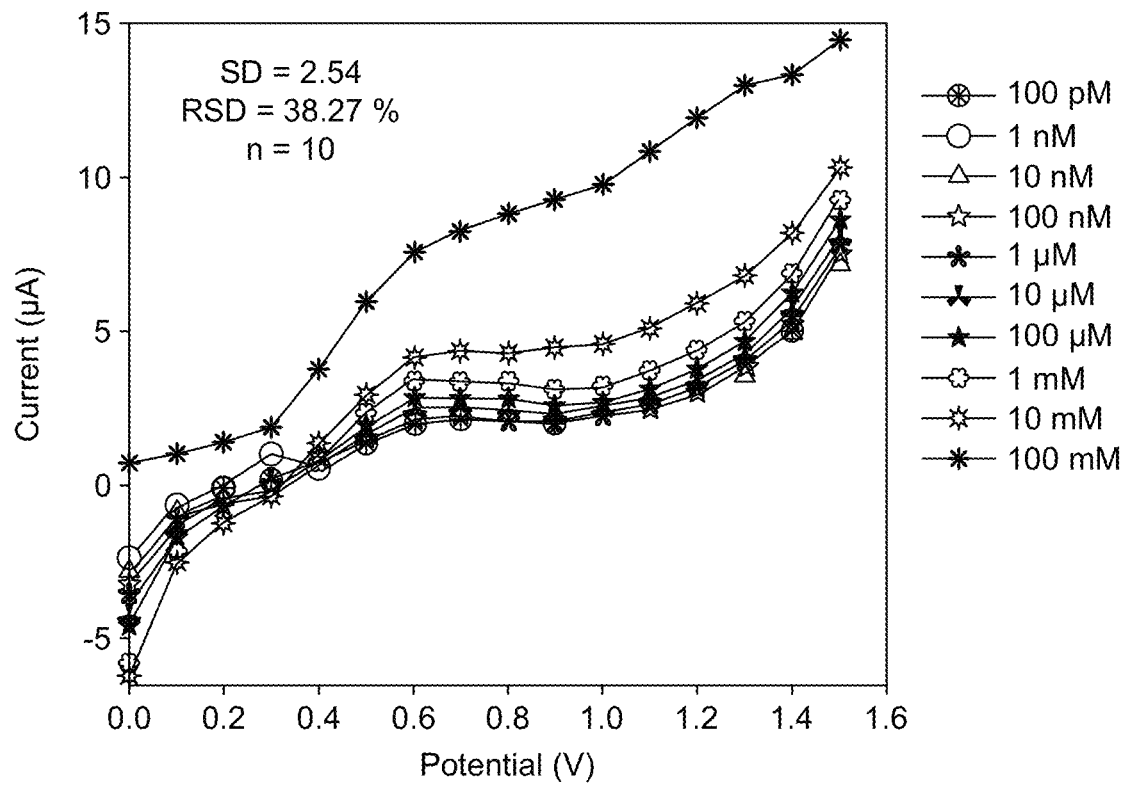
FIG. 11A is an I-V graph depicting the effect of concentration of cadmium ions on current change with the surface modified electrode.
Figure 11B:
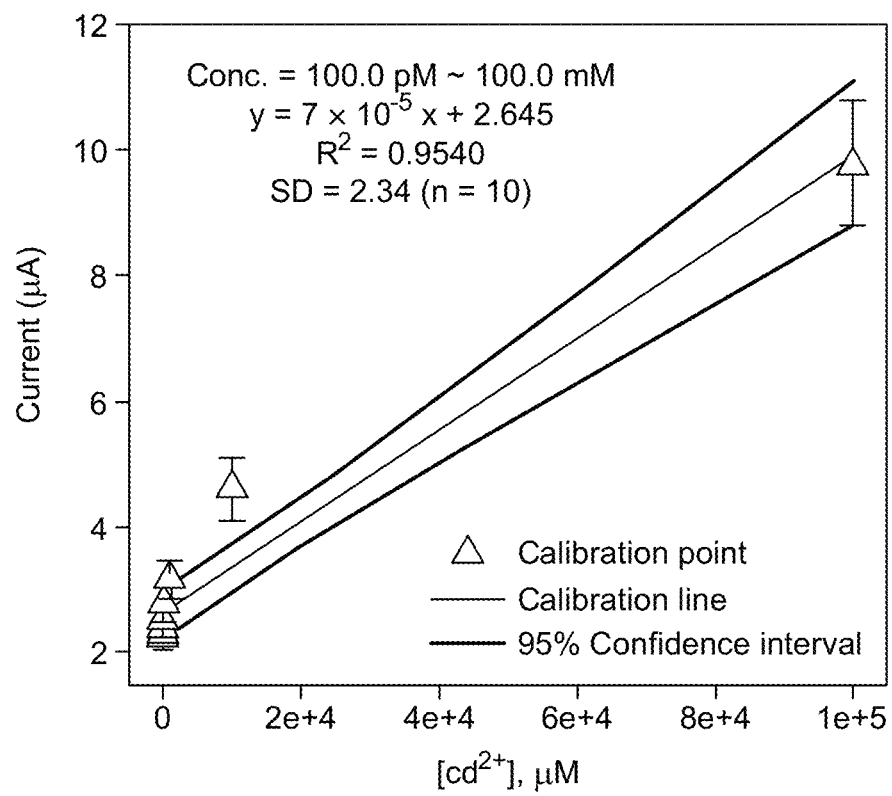
FIG. 11B shows a calibration plot obtained from FIG. 12A vs. cadmium ions concentration.
Figure 11C:
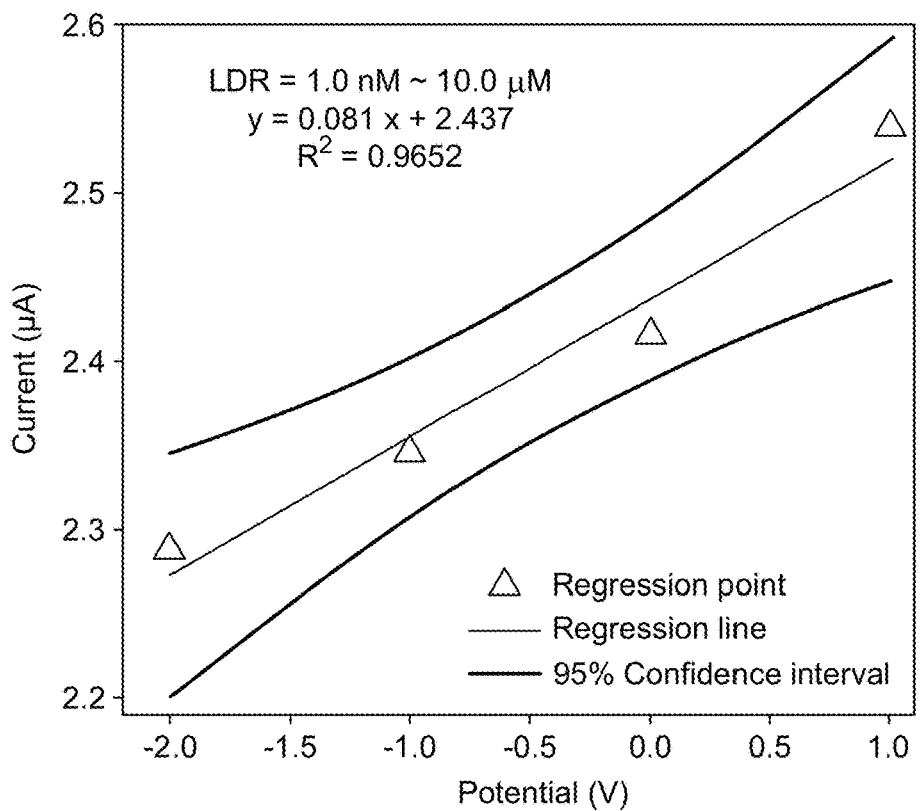
FIG. 11C shows a linear dynamic range plot with an error limit of 10%.
Figure 11D:
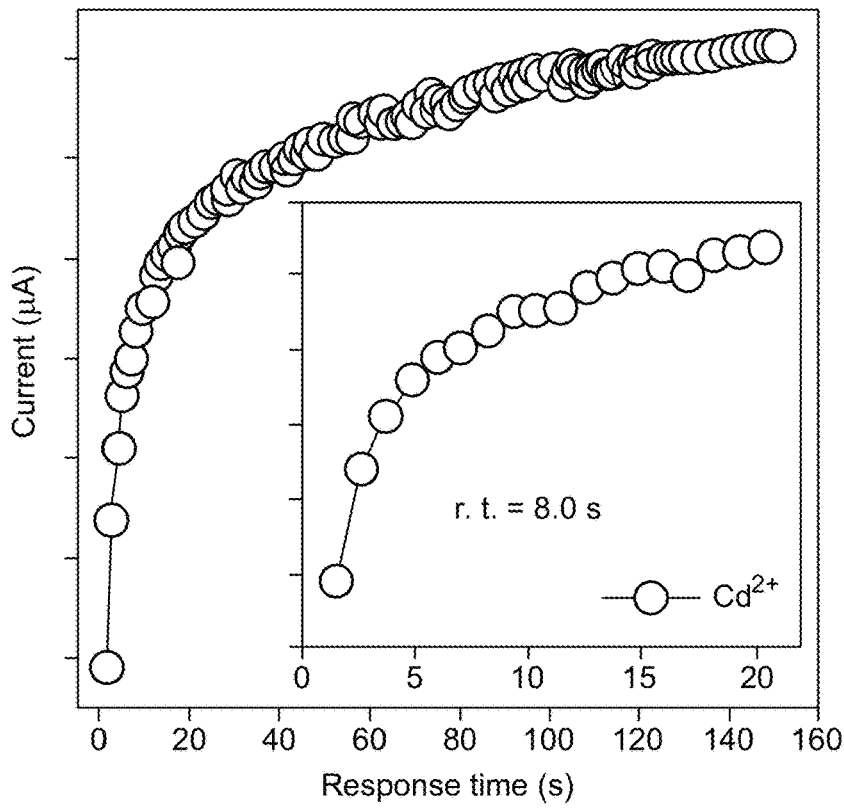
FIG. 11D shows a response time of cadmium ions towards the electrochemical sensor.

FIG. 11A is an I-V graph depicting the effect of concentration of cadmium ion on current change with the surface modified electrode. Electrical signals at various concentrations (100.0 pM~100.0 mM) towards NF/4-BBMBSH/GCE sensor were examined, which is a function of concentration of $Cd^{2+}$ under electrochemical method. It was marked that the change in current response was proportional to the concentration of cadmium ion. In other words, it can be observed from the FIG. 11A that a gradual change in current response was observed by increasing the concentration of $Cd^{2+}$ [SD=2.54, RSD=38.27% at +1.4 V, n=10]. Electrochemical analysis was performed with $Cd^{2+}$ at various concentrations, at an applied potential between 0~+1.5 V to discover the apparent analytical limits. Calibration curve was found linear at +1.0 V ($R^2$=0.9540, SD=2.34, n=10, and error limit=10.0%) at different $Cd^{2+}$ concentrations (FIG. 11B). Sensor parameters such as sensitivity, limit of detection (LOD), and limit of quantification (LOQ) were calculated from calibration curve (+1.0 V) using the equations (i-iii) and found as 2.21519 nAµM$^{-1}$ cm$^{-2}$, 334.29 mM, and 10.03 pM correspondingly. Linear dynamic range, LDR (10.0 nM~10.0 µM) was also found linear ($R^2$=0.9652) from the calibration plot (FIG. 11C). Response time of $Cd^{2+}$ was found 8.0 s at 1.0 µM and 25.0 µL in buffer phase (10.0 mL, pH=6.5, and 100.0 mM) towards NF/4-BBMBSH/GCE sensor (FIG. 11D). Here, electrochemical characteristic of the 4-BBMBSH is analyzed as a function of $Cd^{2+}$ concentration at room conditions, where improved resultant current response at a higher concentration. As obtained, the current response of the NF/4-BBMBSH/GCE film is significantly increased (π-π* interaction) with the increasing concentration of selective $Cd^{2+}$, however similar phenomena for toxic chemical detection have also been reported elsewhere. For a low concentration of $Cd^{2+}$ in liquid medium, there is a smaller surface coverage of $Cd^{2+}$ on NF/4-BBMBSH/GCE film and hence the surface reaction proceeds steadily. By increasing the $Cd^{2+}$ concentration, the surface reaction is increased significantly (gradually increased the response as well) due to active surface area (NF/4-BBMBSH/GCE) contacted with $Cd^{2+}$. Further increasing of $Cd^{2+}$ concentration on MPEBSH/GCE surface, it is exhibited a more rapid increased the current responses, due to larger surface area covered by $Cd^{2+}$ as well as π-π interaction of the nitrogen and oxygen containing functional groups. The π-π interaction could be approaches as inter-molecular and intra-molecular interactions of the 4-BBMBSH.

$$\text{Sensitivity} = \frac{m}{A} \qquad (i)$$

$$LOD = \frac{(3 \times SD)}{m} \qquad (ii)$$

$$LOQ = \frac{(10 \times SD)}{m} \qquad (iii)$$

Evaluation of NF/4-BBMBSH/GCE Sensor Performances

Figure 12A:
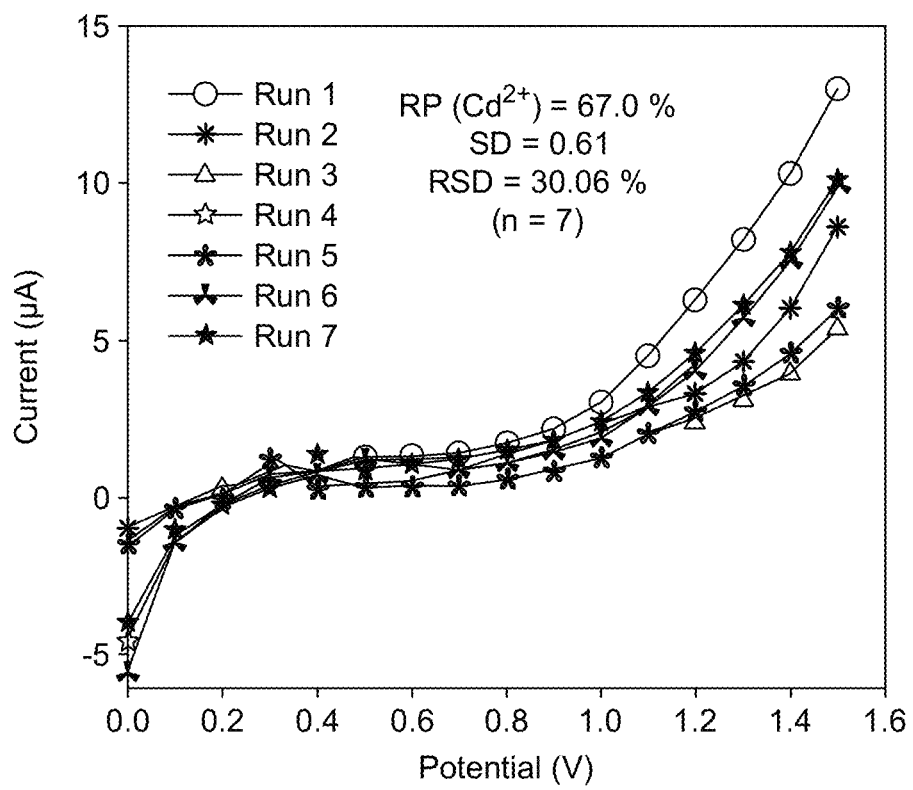
FIG. 12A shows the reproducibility response of the surface modified electrode for sensing cadmium ions.

Sensing efficiency of the NF/4-BBMBSH/GCE sensor was evaluated up to few days regarding estimation of the reproducible (RP) parameter. Consequently, seven successive runs of $Cd^{2+}$ (25.0 µL and 1.0 µM) response was examined at identical conditions in phosphate buffer (10.0 mL, pH=6.5, and 100.0 mM) using different electrodes. Best results were observed with the NF/4-BBMBSH/GCE sensor (RP=67.0%, SD=0.61, RSD=30.06% at +1.0 V, and n=7), the results of which are presented in FIG. 12A and Table 5.

TABLE 5

Sensor probe examination at calibrated potential

| Repli-cates | Current (µA) | Reproducibility, RP (%) | | Current (µA) | Repeatability, RA (%) | |
|---|---|---|---|---|---|---|
| | | Individual | Average | | Individual | Average |
| 1 | 3.00 | 100 | | 1.40 | 100 | |
| 2 | 2.30 | 77 | | 1.26 | 90 | |
| 3 | 1.32 | 44 | | 1.08 | 77 | |
| 4 | 1.85 | 62 | 67 | 1.07 | 76 | 80 |
| 5 | 1.30 | 43 | | 0.98 | 70 | |
| 6 | 1.96 | 65 | | 1.09 | 78 | |
| 7 | 2.39 | 80 | | 0.97 | 69 | |

Here, the reproducibility and repeatability of replicate 1 has been considered to be 100%.

Figure 12B:
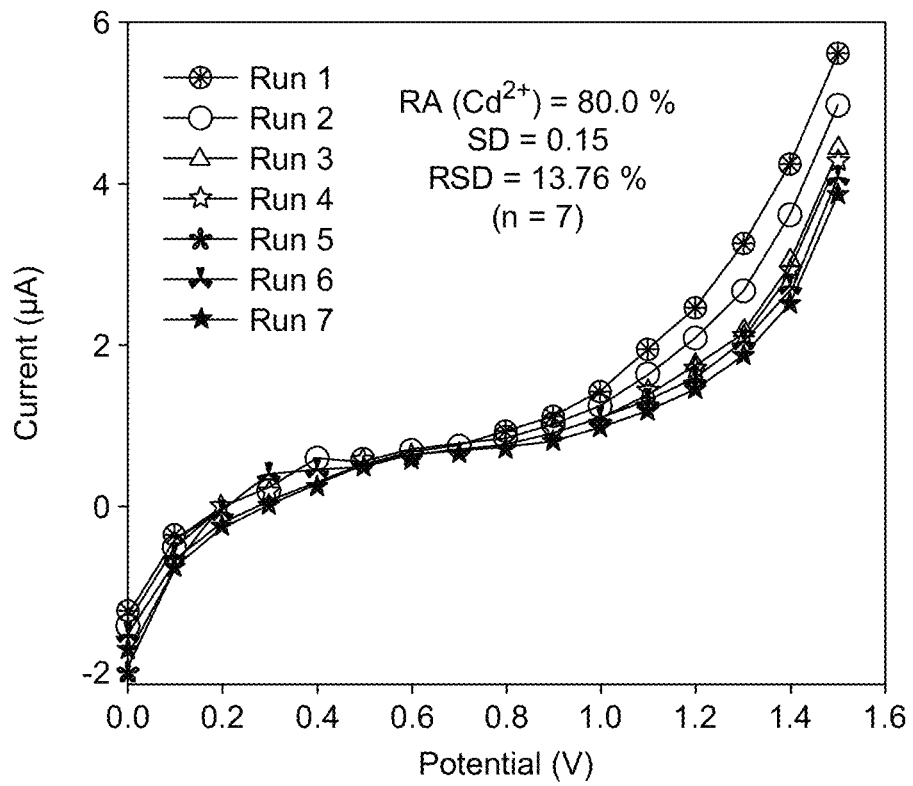
FIG. 12B shows the repeatability response of the surface modified electrode for sensing cadmium ions.

Current responses of the NF/4-BBMBSH/GCE sensor were also measured with respect of storage time for the detection of extended storage susceptibility. An appreciation of storage ability of the NF/4-BBMBSH/GCE sensor was examined at (1.0 µM and ~25.0 µL) in phosphate buffer (10.0 mL, pH=6.5, and 100.0 mM) under standard condition using the surface modified electrode, as well as the repeatability (RA) at calibrated potential (+1.0 V) was found 80.0% towards $Cd^{2+}$, [SD=0.15, RSD=13.76%, and n=7] (FIG. 12B and Table 5).

An analytical parameter (i.e., sensitivity) remained almost similar in each measurement up too few days and after that the responses of the NF/4-BBMBSH/GCE sensor become decreased slowly. It was noticeably reported that the proposed sensor can be used without any primary response in sensitivity up to few days. A comparison of $Cd^{2+}$ detection using different sensors is investigated and presented here in Table 6.

TABLE 6

Detection of $Cd^{2+}$ using different sensor matrix with various recognized methods

| Sensors | Methods | Sensitivity | LOD (μg/L) | LDR (μg/L) |
|---|---|---|---|---|
| $SnO_2QD/GE$ | CV | — | ~500 | 5000-45000 |
| BF/GCE | SWASV | — | 0.3 | 1-170 |
| SB/PME | POT | — | 5.6 | 8.9-11240000 |
| MWCNT-SB/CPE | SWASV | — | 0.74 | 1-1200 |
| Calix[4]arene/PME | POT | — | 179.8 | 179.8-1124000 |
| — | SWASV | — | 1.0 | 10-50 |
| p-allylcalix[4]arene/GCE | DPV | — | 2.2 | 10-300 |
| NDG/GCE | DPSV | — | 3.4 | 5.6-1011 |
| Cd-IIP/CPE | DPASV | — | 0.15 ≈ | 0.5-40 |
| NF/4-BBMBSH/GCE | I-V | 2.21519 ($nA\mu M^{-1}cm^{-2}$) | 10.03 pM | 10.0~10.0 (nM~μM) |

QD: Quantum dots, BF: Bismuth film, SB; Schiff base, CV: Cyclic voltammetry, SWASV: Square wave anodic stripping voltammetry, POT: Potentiometry, DVP: Differential pulse voltammetry, DPSV: Differential pulse stripping voltammetry, DPASV: Differential pulse anodic stripping voltammetry, GE: Gold electrode, GCE: Glassy carbon electrode, PME: Polymeric membrane electrode, CPE: Carbon paste electrode, and I-V: Current-voltage.

Assessment of Interference Effect

Figure 13A:
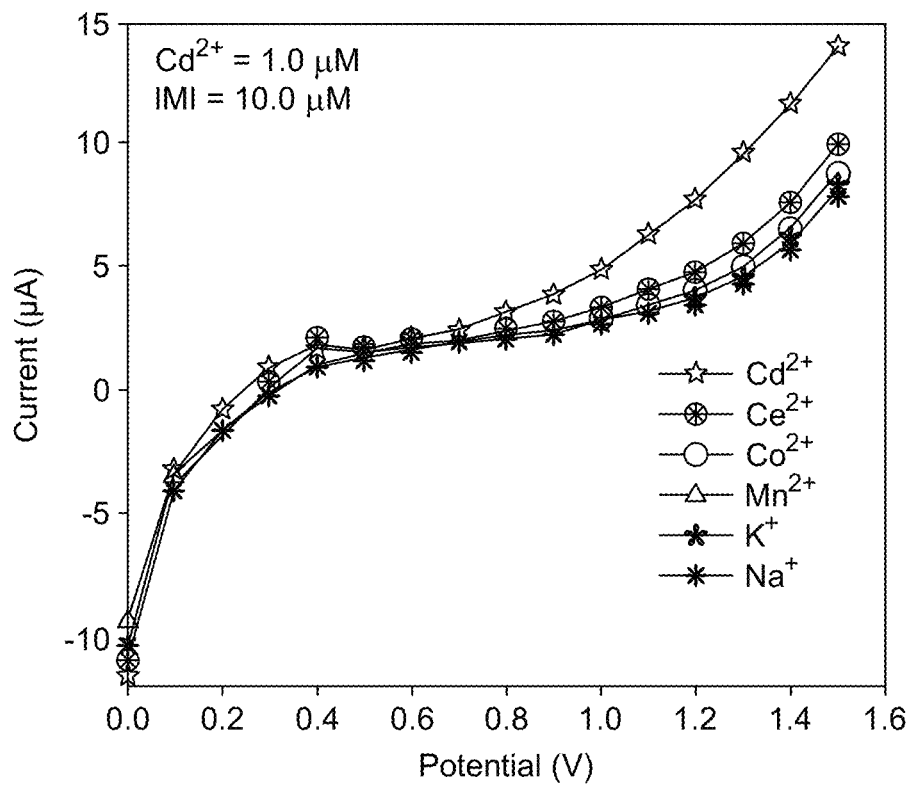
FIG. 13A is a plot depicting interference of other metal ions (interfering metal ions) in detecting cadmium ion with the surface modified electrode.
Figure 13B:
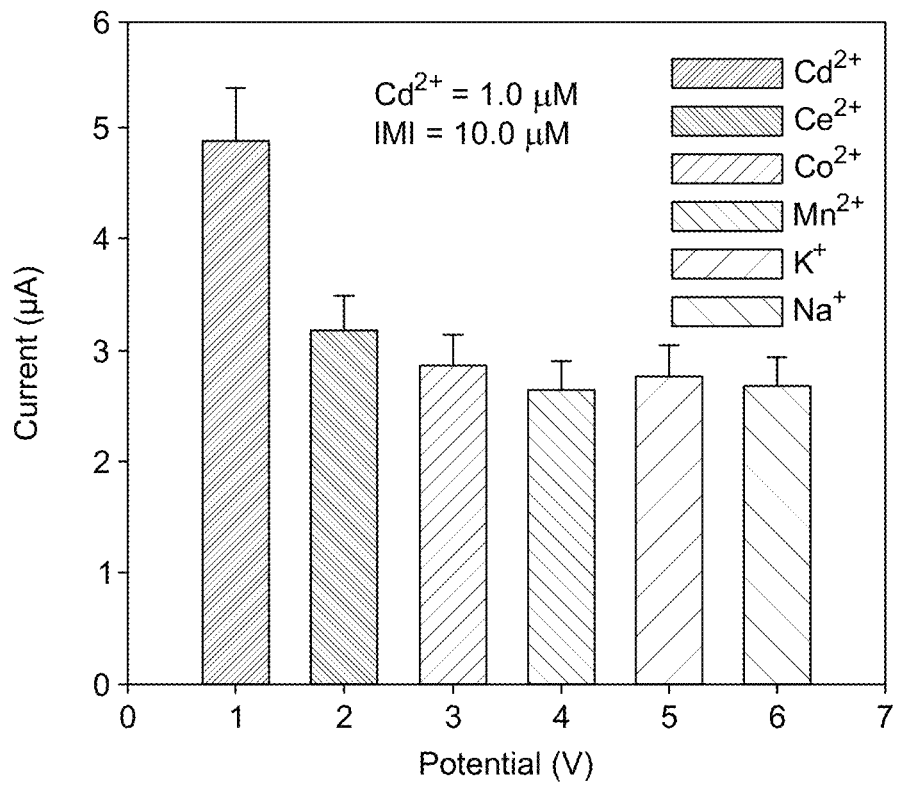
FIG. 13B shows a bar diagram depicting current change response to the interfering metal ions at +1.0 V with an error limit of 10.0%.

FIG. 13A is a plot depicting interference analysis of the surface modified electrode in the presence of other interfering metal ions. Interference examination is one of the most important validation technique in analytical science in order to assess the differences between the interfering metal ions (IMI) having similar cationic nature. $Ce^{2+}$, $Co^{2+}$, $Mn^{2+}$, $K^+$ and $Na^+$ are generally used as IMI in the detection of $Cd^{2+}$ in electrochemically. Current responses of NF/4-BBMBSH/GCE sensor toward the addition of $Cd^{2+}$ (1.0 μM and ~25.0 μL) and IMI such as $Ce^{2+}$, $Co^{2+}$, $Mn^{2+}$, $K^+$ and $Na^+$ (10.0 μM and ~25.0 μL) in PB (10.0 mL, pH=6.5, and 100.0 mM) were examined by using the fabricated electrode. Interference effect of interfering metal ions towards $Cd^{2+}$ was calculated at the calibrated potential (+1.0 V), where the interference effect of $Cd^{2+}$ was considered to be 100.0% (FIG. 13A and Table 7). It was marked that NF/4-BBMBSH/GCE sensor didn't show any notable responses towards the interfering metal ions in identical conditions. Therefore, the proposed sensor (NF/4-BBMBSH/GCE) is good and efficient for the detection of selective $Cd^{2+}$ ions with good results. FIG. 13B shows a bar diagram depicting current change response to the interfering biomolecules at +1.0 V with an error limit of 10.0%.

TABLE 7

Study of interference effect for various metal ions with NF/4-BBMBSH/GCE sensor probe by electrochemical method in identical conditions

| IMI | Observed current (μA) | | | | IEE (%) | SD (n = 3) | RSD % (n = 3) |
|---|---|---|---|---|---|---|---|
| | R1 | R2 | R3 | Average | | | |
| $Cd^{2+}$ | 7.12 | 4.02 | 3.47 | 4.87 | 100 | 1.97 | 40.41 |
| $Ce^{2+}$ | 3.42 | 3.08 | 3.02 | 3.17 | 65 | 0.22 | 6.80 |
| $Co^{2+}$ | 3.00 | 2.81 | 2.77 | 2.86 | 59 | 0.12 | 4.30 |
| $Mn^{2+}$ | 2.86 | 2.56 | 2.51 | 2.64 | 54 | 0.19 | 7.16 |
| $K^+$ | 2.86 | 2.73 | 2.70 | 2.76 | 57 | 0.09 | 3.08 |
| $Na^+$ | 2.75 | 2.64 | 2.62 | 2.67 | 55 | 0.07 | 2.62 |

Examination of Environmental Samples

Figure 14A:
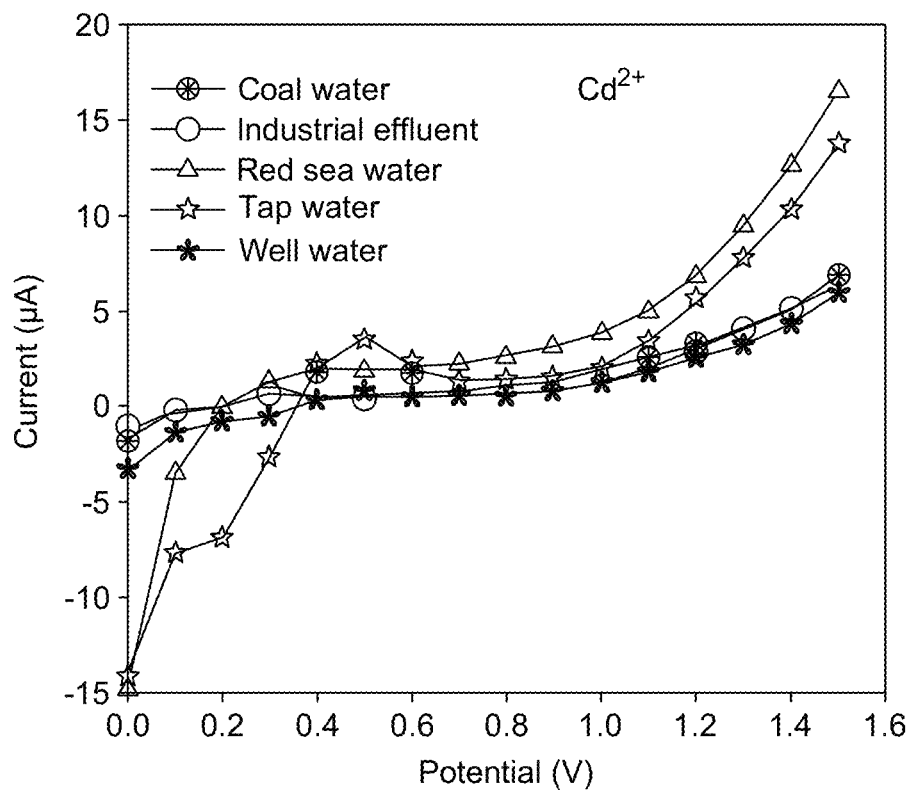
FIG. 14A is an I-V graph determining cadmium ion concentration from various samples with the electrochemical sensor of the present disclosure.
Figure 14B:
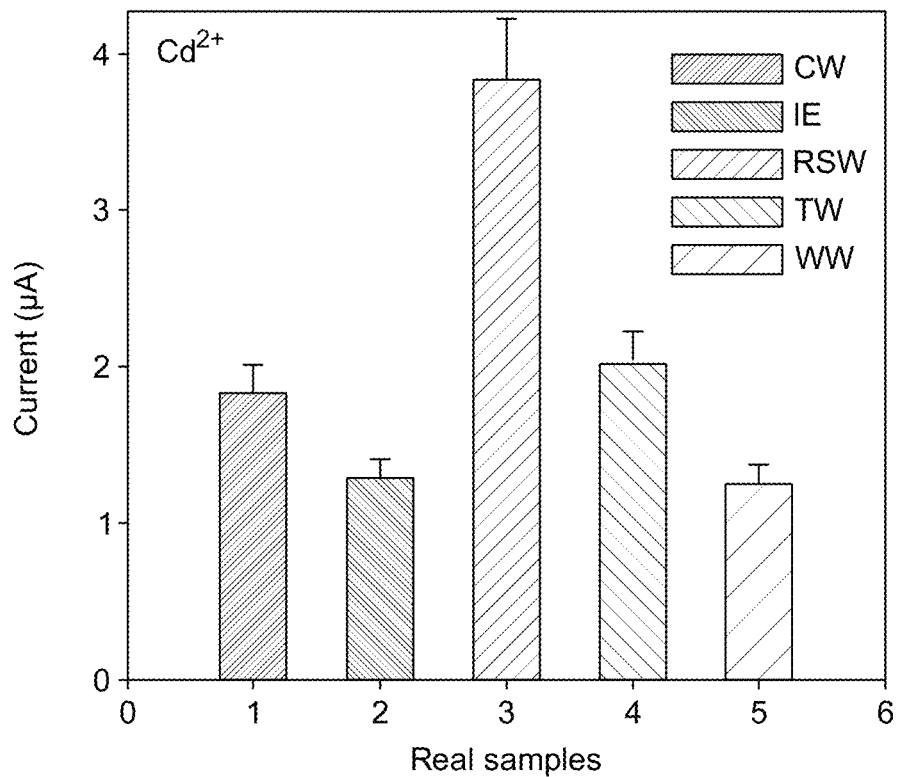
FIG. 14B is a bar diagram determining cadmium ion concentration from various samples with the electrochemical sensor at +1.0 V with an error limit of 10.0%.

FIG. 14A is an I-V graph determining cadmium ion concentration from various samples with the electrochemical sensor of the present disclosure. For this purpose, groups of natural samples such as coal water (CW), industrial effluent (IE), red sea water (RSW), tap water (TW), and well water (WW) were analyzed with NF/4-BBMBSH/GCE sensor for determining cadmium ion concentration in natural samples on the basis of a standard addition technique. A fixed quantity (~25.0 μL) of each natural sample in phosphate buffer phase (10.0 mL, pH=6.5, and 100.0 mM) was analyzed by using the fabricated NF/4-BBMBSH/GCE sensor. Concentration was calculated at the calibrated potential (+1.0 V) for detection of $Cd^{2+}$ in CW, IE, RSW, TW, and WW by the electrochemical method as it is easy, reliable, and acceptable for analyzing of natural samples (FIG. 14B). It was observed that the concentration of cadmium in red sea water was found comparable with other natural samples (FIG. 14A, FIG. 14B and Table 8). The results establish that current-voltage procedure might be a good experimentation tool for the determination of cadmium ion concentration from natural samples.

TABLE 8

Real samples analysis with NF/4-BBMBSH/GCE sensor probe by electrochemical method

| NS | Observed current (μA) | | | | Concentration (μM) | SD (n = 3) | RSD % (n = 3) |
|---|---|---|---|---|---|---|---|
| | R1 | R2 | R3 | Average | | | |
| CW | 2.89 | 1.46 | 1.14 | 1.83 | 0.76 | 0.93 | 50.92 |
| IE | 2.17 | 0.93 | 0.72 | 1.28 | 0.53 | 0.78 | 61.54 |
| RSW | 5.02 | 3.35 | 3.14 | 3.84 | 1.59 | 1.03 | 26.85 |
| TW | 2.03 | 1.94 | 2.08 | 2.02 | 0.83 | 0.07 | 3.52 |
| WW | 2.26 | 0.83 | 0.67 | 1.25 | 0.52 | 0.88 | 69.85 |

NS: Natural samples, CW: Coal water, IE: Industrial effluent, RSW: Red sea water, TW: Tap water, WW: Well water, R: Reading, SD: Standard deviation, and RSD: Relative standard deviation.

INDUSTRIAL APPLICABILITY

The electrochemical sensor of the present disclosure offers several advantages over the prior art for detection of cadmium. One advantage of the embodiments according to the present disclosure is that the electrochemical sensor shows good reliability, reproducibility, and stability under ambient conditions. Also, the sensor shows a better electrical response than the uncoated GEC. Yet another advantage of the embodiments of the present disclosure is the good detectability, high sensitivity, and high selectivity for cadmium ions. Enhanced electro-catalytic property in detecting cadmium, handy nature, good reproducibility, wide LDR, high sensitivity, and low LOD, makes this electrochemical sensor an excellent choice for the detection of cadmium.

It is understood that the examples, embodiments and teachings presented in this application are described merely for illustrative purposes. Any variations or modifications thereof are to be included within the scope of the present application as discussed.

ACKNOWLEDGMENT

The authors extend their appreciation to the Deputyship for Research & Innovation, Ministry of Education in Saudi Arabia for funding this research work through the project number "2021-035" and King Abdulaziz University, DSR, Jeddah, Saudi Arabia.

What is claimed is:

1. A surface modified electrode configured to indicate contact with cadmium ions (Cd$^{+2}$), comprising:
a glassy carbon electrode; and
a coating of a compound of Formula I, bound to the glassy carbon electrode by a polymer matrix, the compound of Formula I carrying a chemical information that changes in response to contact with Cd$^{+2}$ ions, by a change amount that is selective to Cd$^{+2}$ ions relative to interfering ions, the Formula 1 being

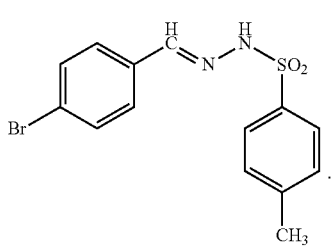

Formula I

2. The surface modified electrode according to claim 1, wherein the polymer matrix is a sulfonated tetrafluoroethylene-based fluoropolymer (nafion).

3. A method of preparing the surface modified electrode according to claim 2, the method comprising:
depositing a slurry of a compound of Formula I on a glassy carbon electrode to form a film; and

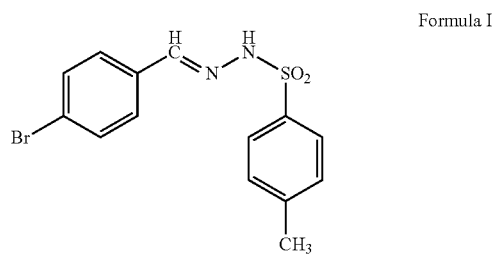

Formula I coating a polymer matrix on the film to obtain the surface modified electrode.

4. The method according to claim 3 further comprising, depositing the slurry of the compound of Formula I on the glassy carbon electrode for a period of 1-4 hours.

5. The method according to claim 3 further comprising, coating the polymer matrix on the film at a temperature range of 35 to 45° C. for a period of 2-4 hours.

* * * * *